US012661108B2

(12) United States Patent　(10) Patent No.:　US 12,661,108 B2
Ruffieux et al.　(45) Date of Patent:　Jun. 23, 2026

(54) DEVICE FOR CLOSING A TISSUE OPENING

(71) Applicant: UNIVERSITÄT ZÜRICH, Zürich (CH)

(72) Inventors: Kurt Ruffieux, Thalwil (CH); Yannick Devaud, Zürich (CH); Mathias Blaser, Zürich (CH); Sebastian Wollmann, Nussbaumen (CH); Marko Rusov, Belgrade (RS); Nicole Ochsenbein-Kölble, Zürich (CH); Martin Ehrbar, Wil (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 77 days.

(21) Appl. No.: 18/717,099

(22) PCT Filed: Nov. 21, 2022

(86) PCT No.: PCT/EP2022/082621
§ 371 (c)(1),
(2) Date: Jun. 6, 2024

(87) PCT Pub. No.: WO2023/104486
PCT Pub. Date: Jun. 15, 2023

(65) Prior Publication Data
US 2025/0040922 A1　Feb. 6, 2025

(30) Foreign Application Priority Data

Dec. 6, 2021　(EP) .................................... 21212537

(51) Int. Cl.
*A61B 17/04*　(2006.01)
*A61B 17/06*　(2006.01)
*A61B 17/42*　(2006.01)

(52) U.S. Cl.
CPC ...... *A61B 17/0469* (2013.01); *A61B 17/0482* (2013.01); *A61B 17/06004* (2013.01);
(Continued)

(58) Field of Classification Search
CPC . A61B 17/42; A61B 17/0469; A61B 17/0482; A61B 17/06004
See application file for complete search history.

(56) References Cited

U.S. PATENT DOCUMENTS 4,608,965 A　9/1986　Anspach, Jr. et al.
4,779,616 A　10/1988　Johnson
(Continued)

FOREIGN PATENT DOCUMENTS

CN　105962979 A　9/2016
CN　106264630 A　1/2017
(Continued)

OTHER PUBLICATIONS

Extended Search Report in corresponding European patent application No. 21212537.1 dated Feb. 6, 2022.
(Continued)

*Primary Examiner* — Tuan V Nguyen
(74) *Attorney, Agent, or Firm* — Westman, Champlin & Koehler, P.A.

(57)　ABSTRACT

The invention relates to a device to be used for closing a tissue opening in a tissue. In particular, the present invention relates to a device used for a closing an opening in a membrane such as a fetal membrane by stitching in a minimally invasive procedure.

27 Claims, 19 Drawing Sheets

(52) U.S. Cl.
CPC ...... *A61B 17/42* (2013.01); *A61B 2017/0472* (2013.01); *A61B 2017/06042* (2013.01); *A61B 2017/4216* (2013.01)

(56) References Cited

U.S. PATENT DOCUMENTS

| | | | |
|---|---|---|---|
| 5,330,488 A | 7/1994 | Goldrath |
| 5,496,332 A | 3/1996 | Sierra et al. |
| 5,501,691 A | 3/1996 | Goldrath |
| 5,507,755 A | 4/1996 | Gresl et al. |
| 5,562,688 A | 10/1996 | Riza |
| 5,755,727 A | 5/1998 | Kontos |
| 5,830,232 A | 11/1998 | Hasson |
| 5,860,990 A | 1/1999 | Nobles et al. |
| 5,984,948 A | 11/1999 | Hasson |
| 6,074,404 A | 6/2000 | Stalker et al. |
| 6,117,144 A | 9/2000 | Nobles et al. |
| 6,398,796 B2 | 6/2002 | Levinson |
| 6,562,052 B2 | 5/2003 | Nobles et al. |
| 6,605,096 B1 | 8/2003 | Ritchart |
| 7,060,077 B2 | 6/2006 | Gordon et al. |
| 7,232,448 B2 | 6/2007 | Battles et al. |
| 7,544,199 B2 | 6/2009 | Bain et al. |
| 7,758,597 B1 | 7/2010 | Tran et al. |
| 7,766,925 B2 | 8/2010 | Stokes et al. |
| 7,976,553 B2 | 7/2011 | Shelton, IV et al. |
| 7,993,354 B1 | 8/2011 | Brecher et al. |
| 8,105,342 B2 | 1/2012 | Onuki et al. |
| 8,123,764 B2 | 2/2012 | Meade et al. |
| 8,197,510 B2 | 6/2012 | Nobles |
| 8,449,559 B2 | 5/2013 | Keren et al. |
| 8,469,975 B2 | 6/2013 | Nobles et al. |
| 8,496,676 B2 | 7/2013 | Nobles et al. |
| 8,709,020 B2 | 4/2014 | Nobles |
| 8,926,640 B2 | 1/2015 | Sauer et al. |
| 8,992,549 B2 | 3/2015 | Bennett, III |
| 9,398,907 B2 | 7/2016 | Nobles et al. |
| 9,492,162 B2 | 11/2016 | Murillo et al. |
| 9,554,792 B1 | 1/2017 | Nobles et al. |
| 9,675,342 B2 | 6/2017 | Prior et al. |
| 9,795,375 B2 | 10/2017 | Lore et al. |
| 9,895,146 B1 | 2/2018 | Al-Jazaeri |
| 9,962,152 B2 | 5/2018 | Meade et al. |
| 10,045,871 B2 | 8/2018 | Saadat et al. |
| 10,182,802 B2 | 1/2019 | Nobles et al. |
| 10,413,296 B2 | 9/2019 | Prior et al. |
| 10,420,545 B2 | 9/2019 | Nobles et al. |
| 10,512,458 B2 | 12/2019 | Nobles |
| 2002/0013571 A1 | 1/2002 | Goldfarb et al. |
| 2002/0045908 A1 | 4/2002 | Nobles et al. |
| 2002/0095164 A1 | 7/2002 | Andreas et al. |
| 2003/0109891 A1 | 6/2003 | Dana et al. |
| 2003/0216756 A1 | 11/2003 | Klein et al. |
| 2004/0044365 A1 | 3/2004 | Bachman |
| 2004/0049207 A1 | 3/2004 | Goldfarb et al. |
| 2004/0068273 A1 | 4/2004 | Fariss et al. |
| 2004/0143294 A1 | 7/2004 | Corcoran et al. |
| 2004/0225301 A1 | 11/2004 | Roop et al. |
| 2005/0000437 A1 | 1/2005 | Tomblerm, Jr. et al. |
| 2005/0121042 A1 | 6/2005 | Belhe et al. |
| 2005/0149066 A1 | 7/2005 | Stafford |
| 2006/0030868 A1 | 2/2006 | Bennett, III |
| 2007/0093859 A1 | 4/2007 | Phillips |
| 2007/0118151 A1 | 5/2007 | Davidson |
| 2007/0149987 A1 | 6/2007 | Wellman et al. |
| 2007/0179507 A1 | 8/2007 | Shah |
| 2007/0213757 A1 | 9/2007 | Boraiah |
| 2008/0045979 A1 | 2/2008 | Ma |
| 2008/0045980 A1 | 2/2008 | Schwarz |
| 2008/0065156 A1 | 3/2008 | Hauser et al. |
| 2008/0154286 A1 | 6/2008 | Abbott et al. |
| 2008/0249545 A1 | 10/2008 | Shikhman |
| 2009/0062852 A1 | 3/2009 | Marino |
| 2009/0234295 A1 | 9/2009 | Lampropoulos et al. |

| | | | |
|---|---|---|---|
| 2010/0016870 A1* | 1/2010 | Campbell .............. A61B 17/04 606/144 |
| 2010/0130990 A1 | 5/2010 | Saliman |
| 2010/0198235 A1 | 8/2010 | Pierce et al. |
| 2010/0318107 A1 | 12/2010 | Mizrahy et al. |
| 2011/0112553 A1 | 5/2011 | Smith |
| 2011/0190793 A1 | 8/2011 | Nobles et al. |
| 2011/0245850 A1 | 10/2011 | van der Burg et al. |
| 2012/0209300 A1 | 8/2012 | Torrie |
| 2012/0296373 A1 | 11/2012 | Roorda et al. |
| 2013/0035699 A1 | 2/2013 | Heneveld et al. |
| 2013/0116708 A1 | 5/2013 | Ziniti et al. |
| 2013/0165956 A1 | 6/2013 | Sherts et al. |
| 2013/0245644 A1 | 9/2013 | Tegels |
| 2013/0253543 A1 | 9/2013 | Heneveld |
| 2013/0310856 A1 | 11/2013 | Sherts et al. |
| 2014/0039528 A1 | 2/2014 | Torrie |
| 2014/0039529 A1 | 2/2014 | Torrie |
| 2014/0039530 A1 | 2/2014 | Torrie |
| 2014/0128887 A1 | 5/2014 | Argentine |
| 2014/0148825 A1 | 5/2014 | Nobles et al. |
| 2014/0171981 A1 | 6/2014 | Jimenez et al. |
| 2014/0222035 A1 | 8/2014 | Chu |
| 2014/0257344 A1 | 9/2014 | Tegels |
| 2014/0276974 A1 | 9/2014 | Escobar et al. |
| 2014/0276979 A1 | 9/2014 | Sauer et al. |
| 2014/0350576 A1 | 11/2014 | Patel et al. |
| 2015/0038991 A1 | 2/2015 | Prior et al. |
| 2015/0223804 A1 | 8/2015 | Wu et al. |
| 2015/0313583 A1 | 11/2015 | Heneveld |
| 2015/0342582 A1 | 12/2015 | Heneveld |
| 2016/0220238 A1 | 8/2016 | Heneveld |
| 2016/0345965 A1 | 12/2016 | Ho et al. |
| 2017/0020511 A1* | 1/2017 | Roorda .............. A61B 17/0469 |
| 2017/0049435 A1 | 2/2017 | Sauer et al. |
| 2017/0119384 A1 | 5/2017 | Stokes et al. |
| 2017/0231624 A1 | 8/2017 | Sniffin et al. |
| 2017/0238922 A1 | 8/2017 | Heneveld |
| 2018/0085130 A1 | 3/2018 | Fung et al. |
| 2018/0168569 A1 | 6/2018 | Nobles et al. |
| 2018/0235603 A1 | 8/2018 | Heneveld |
| 2018/0271516 A1 | 9/2018 | Sauer |
| 2018/0344313 A1 | 12/2018 | Heneveld |
| 2019/0209161 A1 | 7/2019 | Brecher et al. |
| 2019/0254646 A1 | 8/2019 | Heneveld |
| 2019/0261996 A1 | 8/2019 | Goldfarb et al. |
| 2019/0298336 A1 | 10/2019 | Sauer |
| 2020/0046343 A1 | 2/2020 | Kramer |
| 2020/0214694 A1 | 7/2020 | Nobles |

FOREIGN PATENT DOCUMENTS

| | | |
|---|---|---|
| CN | 106725667 A | 5/2017 |
| CN | 106214196 B | 12/2018 |
| CN | 105748121 B | 6/2020 |
| DE | 19944236 A1 | 3/2001 |
| EP | 0537758 A1 | 4/1993 |
| EP | 0941698 A1 | 9/1999 |
| EP | 1598017 A1 | 11/2005 |
| EP | 1757234 A1 | 2/2007 |
| EP | 1155418 B1 | 11/2007 |
| EP | 1683487 B1 | 2/2008 |
| EP | 2138108 A1 | 12/2009 |
| EP | 2236094 A2 | 10/2010 |
| EP | 2305129 A2 | 4/2011 |
| EP | 2394585 A1 | 12/2011 |
| EP | 3222219 A1 | 9/2017 |
| EP | 3308721 A1 | 4/2018 |
| EP | 3420983 A1 | 1/2019 |
| EP | 2412317 B1 | 7/2019 |
| EP | 2697721 B1 | 9/2019 |
| EP | 3563775 A1 | 11/2019 |
| EP | 3569160 A1 | 11/2019 |
| EP | 3420985 B1 | 5/2021 |
| JP | H05161655 A | 6/1993 |
| JP | 2007252404 A | 10/2007 |
| JP | 2012249927 A | 12/2012 |
| WO | 9629012 A1 | 9/1996 |
| WO | 9631165 A1 | 10/1996 |

(56)        References Cited

FOREIGN PATENT DOCUMENTS

| WO | 9703613 | A1 | 2/1997 |
|----|---------|----|--------|
| WO | 9815309 | A1 | 4/1998 |
| WO | 9925254 | A1 | 5/1999 |
| WO | 0051498 | A1 | 9/2000 |
| WO | 0134035 | A1 | 5/2001 |
| WO | 03065903 | A1 | 8/2003 |
| WO | 03099137 | A2 | 12/2003 |
| WO | 2007139785 | A2 | 12/2007 |
| WO | 2008097068 | A1 | 8/2008 |
| WO | 2008147555 | A2 | 12/2008 |
| WO | 2009026079 | A1 | 2/2009 |
| WO | 2010081096 | A2 | 7/2010 |
| WO | 2010105046 | A1 | 9/2010 |
| WO | 2010141695 | A1 | 12/2010 |
| WO | 2012112424 | A1 | 8/2012 |
| WO | 2012135806 | A1 | 10/2012 |
| WO | 2012142338 | A2 | 10/2012 |
| WO | 2012148265 | A1 | 11/2012 |
| WO | 2012158878 | A2 | 11/2012 |
| WO | 2013003228 | A1 | 1/2013 |
| WO | 2013103682 | A2 | 7/2013 |
| WO | 2013138140 | A1 | 9/2013 |
| WO | 2013170081 | A1 | 11/2013 |
| WO | 2014205279 | A1 | 12/2014 |
| WO | 2015074040 | A1 | 5/2015 |
| WO | 2017070312 | A1 | 4/2017 |
| WO | 2018031804 | A1 | 2/2018 |
| WO | 2018236822 | A1 | 12/2018 |
| WO | 2019103615 | A2 | 5/2019 |
| WO | 2021216809 | A2 | 10/2021 |

OTHER PUBLICATIONS

International Search Report and Written Opinion in corresponding International Application No. PCT/EP2022/082621 dated Mar. 6, 2023.

* cited by examiner

DEVICE FOR CLOSING A TISSUE OPENING

CROSS-REFERENCE TO RELATED APPLICATION(S)

This Application is a Section 371 National Stage Application of International Application No. PCT/EP2022/082621, filed Nov. 21, 2022 and published as WO 2023/104486 A1 on Jun. 15, 2023, in English, and claims priority to European Application No. 21212537.1, filed Dec. 6, 2021.

BACKGROUND OF THE INVENTION

The invention relates to a device to be used for closing a tissue opening in a tissue. In particular, the present invention relates to a device used for a closing an opening in a membrane such as a fetal membrane by stitching in a minimally invasive procedure.

The fetal membrane is a relatively thin tissue layer having a thickness of a few hundred microns that surrounds the fetus during development. The fetal membrane holds amniotic fluid and creates a physical barrier, for example, to protect the fetus from infections and to provide paracrine signaling between the mother and the embryo. Intact fetal membranes are of central importance to a pregnancy. Preterm pre-labor rupture of fetal membranes (PPROM) initiates delivery in most cases, which is a serious complication in early pregnancy. Indeed, preterm birth carries a big risk of complication ranging from incurable diseases decreasing life quality and/or expectancy and range from cerebral palsy, impaired cognitive skills, vision problems, hearing problems, behavioral, psychological as well as chronic health issues to morbidity.

With advances in fetal diagnosis and therapies, fetoscopy has become a clinical routine. This surgical technique aims at treating potentially life-threatening diseases during pregnancy by invasive intervention into the amniotic cavity. Example medical indications include twin-to-twin transfusion syndrome (TTTS), discordant monochorionic twins with a lethal anomaly, reverse arterial perfusion (TRAP) as well as severe congenital diaphragmatic hernia (CDH). Depending on the type of intervention, the injury or perforation created by the fetoscopy can induce iatrogenic PPROM (iPPROM) in 30 to 80% of the cases. This unsolved clinical problem compromises benefits of the surgical intervention and blocks tremendously the advances in treatment technologies.

There is a need to prevent iatrogenic preterm premature rupture of the fetal membrane. In open fetal surgery, the fetal membrane is attached to the uterus along the surgical opening in order to avoid large scale detachment from the uterus. Following the surgery on the fetus, the uterus is closed using sutures, typically resorbable sutures. Minimal invasive approaches show to be beneficial. The limited size of the incision can significantly reduce the wound healing time, pain and remaining scar. However, there is no procedure available to attach the fetal membrane to the uterus and close the tissue defect created by the access puncture in such minimal invasive approaches, where the surgery is performed through a sheath introducer.

Devices for stitching a tissue opening in minimally invasive procedures are known in different areas of medical fields. Prior art stitching devices are known, for example, from EP2 697 721 B1, which relates to suturing devices for suturing an anatomic valve. EP 2 412 317 B1 relates to a wound closure device for suturing an opening in tissue. U.S. Pat. No. 8,992,549 B2 relates to intra-abdominal suturing devices designed for closing puncture wounds created by surgical trocars and similar puncturing devices. U.S. Pat. No. 10,413,296 B2 relates to devices, systems, and methods for closing a wound or opening in tissue.

However, it is noted that the special circumstances of individual surgeries differ in respective documents and the application as in the present invention, e.g., closing a tissue opening of a fetal membrane, is not generally considered. Devices that are better adapted for this purpose would thus be desirable. Moreover, it is believed that such devices may also offer advantages for closing tissue openings in other parts of the body.

It is desired for such devices to be easily operable so that the closure of the tissue opening can be performed by a user more intuitively and consistently. Furthermore, reducing the complexity of the procedure for the user is intended in terms of performing an accurate and fail-safe operation. The operation ideally becomes less dependent on the skills or experience of the user. By designing the device in a more simplistic manner, thereby not necessarily requiring additional supporting equipment, e.g., endoscopy cameras for visualization, the overall costs related to the operation can be also reduced.

Disclosed embodiments of the present invention provide an improved device for closing a tissue opening in a tissue with at least one suture. More specifically, disclosed embodiments of the present invention provide a device for closing a tissue opening or a perforation resulting from a fetoscopy.

SUMMARY OF THE INVENTION

According to a first aspect of the present invention, a device for closing a tissue opening in a tissue with at least one suture is disclosed. The tissue extends at least partially around a body cavity and comprises at least first and second tissue layers, the second tissue layer extending between the first tissue layer and the body cavity. The first tissue layer may be a fascia. The second tissue layer may be a uterus.

The device according to this first aspect comprises an elongate shaft having a proximal end, a distal end and extending along a longitudinal axis, the elongate shaft configured to be inserted into the tissue opening in the tissue, the elongate shaft comprising a plurality of needle guides, each needle guide having a exit opening at its distal end; a support structure at the distal end of the elongate shaft configured to move between a first, contracted configuration and a second, expanded configuration the support structure being configured to be expanded in the body cavity; at least one first needle and at least one second needle; at least one first connector and at least one second connector coupled to the support structure, the first connector being configured to couple with the first needle, optionally with a distal end of thereof, and the second connector being configured to couple with the second needle, optionally with a distal end thereof. Each of the needles is configured to be translated along a respective one of the needle guides, the first needle being configured to be advanced out of the exit opening of the respective needle guide and to penetrate through the tissue, optionally through the second tissue layer and/or not through the first tissue layer, along a first trajectory, the first trajectory extending from the exit opening through the tissue obliquely to the longitudinal axis to the first connector, and the second needle being configured to be advanced out of the exit opening of the respective needle guide and to penetrate through the tissue, optionally through the second tissue layer and/or not through the first tissue layer, along a second trajectory, the second trajectory extending from the exit opening through the second tissue layer obliquely to the longitudinal axis to the second connector. The device also comprises at least one expandable pushing member configured to push the first tissue layer out of the first and second trajectories, the pushing member being configured to move between a contracted configuration and an expanded configuration.

Optionally, the needles penetrate the tissue from outside of the body cavity towards the inside. It is believed that this may help to provide for a simpler and safer actuation mechanics.

The support structure optionally provides the stability and the functionality to connect the connectors with the needles.

The motion of the expandable pushing member pushing the first layer out of the first and second trajectories optionally allows the needle to penetrate only through the second tissue layer of the tissue. Optionally, the pushing member pushes away the overlaying first tissue layer, e.g., fascia, to prevent the first tissue layer from being penetrated by the needles. As a result, the undesired stitching that would connect the first tissue layer and the second tissue layer can be avoided, which may otherwise cause medical complications, e.g., in case of a patient during pregnancy, by the uneven expansion of the tissue layers surrounding the womb.

According to a second aspect of the present invention, a device for closing a tissue opening in a tissue with at least one suture is disclosed. The tissue extends at least partially around a body cavity and optionally comprises at least first and second tissue layers, the second tissue layer extending between the first tissue layer and the body cavity. The first tissue layer may be a fascia. The second tissue layer may be a uterus.

The device according to this second aspect comprises an elongate shaft having a proximal end, a distal end and extending along a longitudinal axis, the elongate shaft configured to be inserted into the opening in the tissue, the elongate shaft comprising a plurality of needle guides, each needle guide having an exit opening at its distal end; a support structure at the distal end of the elongate shaft configured to move between a first, contracted configuration and a second, expanded configuration the support structure being configured to be expanded in the body cavity; at least one first needle and at least one second needle; at least one first connector and at least one second connector coupled to the support structure, the first connector being configured to couple with a distal end of the first needle and the second connector being configured to couple with a distal end of the second needle. Each of the needles is configured to be translated along a respective one of the needle guides, the first needle is configured to be advanced out of the exit opening of the respective needle guide and to penetrate through the tissue, optionally through the second tissue layer, along a first trajectory, the first trajectory extending from the exit opening through the tissue obliquely to the longitudinal axis to the first connector, and the second needle is configured to be advanced out of the exit opening of the respective needle guide and to penetrate through the tissue, optionally through the second tissue layer, along a second trajectory, the second trajectory extending from the exit opening through the second tissue layer obliquely to the longitudinal axis to the second connector. The device also comprises at least one expandable guide member configured to guide the at least one first and the at least one second needles along their respective trajectory, the guide member being configured to move between a contracted configuration and an expanded configuration, wherein the guide member overlaps with the first and second trajectories in the expanded configuration.

The expandable guide member is useful to guide and reinforce at least one first and the at least one second needles along their respective trajectory, which increases the overall accuracy and stability of the needles in moving from the exit openings to their respective connectors. Thereby, undesired deviations of the needles in their advancements towards the connectors may be avoided.

The device according to the first aspect of the present invention may further comprise at least one expandable guide member configured to guide the at least one first and the at least one second needles along their respective trajectory, the expandable guide member being configured to move between a contracted configuration and an expanded configuration, wherein the guide member overlaps with the first and second trajectories in the expanded configuration.

Vice versa, the device according to the second aspect of the present invention may comprise at least one expandable pushing member configured to push the first tissue layer out of the first and second trajectories, the pushing member being configured to move between a contracted configuration and an expanded configuration.

In case of a fetoscopy, the fetal membrane (i.e., a third tissue layer) may be attached to the second tissue layer, e.g., uterus. As the skilled reader will recognize, in other interventions a different third tissue layer may be present that is attached to the second tissue layer or no such third tissue layer may be present at all. Furthermore, instead or in addition to such third tissue layer, an artificial sheath may be positioned in the cavity and attached to the second tissue layer.

The expandable guide member and the expandable pushing member may be combined and/or integrated into a single sub-component and/or into a single expandable sub-assembly of the device. This may provide for a space-saving design, which is particularly advantageous for e.g. fetoscopy, but the devices disclosed herein are not limited in this regard. Depending on the chosen application, providing the expandable guide member and the expandable pushing member as separate sub-assemblies is also considered. For example, the expandable pushing member and the expandable guide member may be provided at the same or at different positions along the longitudinal axis of the elongate shaft.

Moreover, depending on the particular application, the dimensions of the device may be adapted. For example, if the tissue layers are thicker, e.g., due to obesity, the dimensions of the device may be adapted accordingly. The skilled person will thus appreciate that fetoscopy is one application in which the devices according to the present invention may be employed. However, use of the devices for closing other tissue openings is also considered. The dimensions of respective features of the device may be adjusted accordingly based on the teachings of the present invention.

In accordance with all of the above-mentioned aspects, the first and second trajectories may be partially in a cavity created between the pushing member and the elongate shaft.

As a result, each of the needles can move within the cavity created between the elongate shaft and the pushing member, thereby preventing the contact between the needles and the first tissue layer.

the elongate shaft may have a length of not more than 500 mm, not more than 300 mm, or not more than 200 mm. For example, the elongate shaft may have a length between 10 mm to 2000 mm, optionally between 50 mm to 500 mm, optionally between 100 mm to 200 mm.

In accordance with all of the above-mentioned aspects, it is preferred that the elongate shaft is rigid and/or is straight along the longitudinal axis. Optionally, the elongate shaft has a diameter smaller than 15 mm, optionally a diameter smaller than 7 mm, optionally a diameter smaller than 4 mm.

The elongate shaft may comprise a lumen extending along the longitudinal axis. The lumen may have a diameter smaller than 10 mm, optionally a diameter smaller than 7 mm, optionally a diameter smaller than 4 mm. Alternatively or additionally, the lumen may have a diameter larger than 0.1 mm, optionally a diameter larger than 0.25 mm, optionally a diameter larger than 0.5 mm. The lumen may extend from the proximal end to the distal end of the elongate shaft. Optionally, the elongate shaft is made from a mechanically stiff material with an elastic modulus of at least 100 GPa, optionally at least 210 GPa, optionally from a metallic material (such as stainless steel, e.g. 316L or 17-7 steel) or a stiff polymeric material (such as fibre reinforced polymers).

Apart from the application for the fetal membrane, the device can be used for further operations, e.g., transaortic heart surgery, as a catheter-based device. The size dimensions of the elongate shaft with the lumen as described above are considered most appropriate and effective for the use in closing a tissue opening, in particular for the closure of a tissue opening in a fetal membrane.

The device may further comprise a handle at the proximal end of the elongate shaft. The handle may be adapted for allowing the operator to hold the device in a manner that is convenient for the respective application. The handle may comprise measurement indicator lines to provide the user with visual information regarding the positioning of the instrument within the cavity or how far the at least one suture is inserted.

The device may further comprise at least one actuator, optionally a plurality of actuators, at the proximal end of the elongate shaft, optionally at the handle. The actuators may be used for operating the expandable pushing member and/or the expandable guide member, for advancing and/or retracting the needles, for advancing and/or retracting a suture, and/or for injecting at least one fluid through a hollow needle.

The device comprises a distal end. The distal end optionally is atraumatic. The distal end may be formed by the distal end of the elongate shaft, which may be atraumatic (e.g. hemispherical or rounded). Furthermore, the longitudinal axis of the elongate shaft may be configured to be oriented substantially perpendicular to the tissue when closing the tissue opening. The atraumatic end of the elongate shaft reduces the risk of potential damages that may be caused by unintentional contact, e.g. with a foetus.

The needle guides may have a diameter smaller than 2 mm, optionally a diameter smaller than 1 mm, optionally a diameter smaller than 0.5 mm. Alternatively or additionally, the needle guides may have a diameter larger than 0.1 mm, optionally a diameter larger than 0.2 mm, optionally a diameter larger than 0.4 mm.

The size dimensions of the needle guides as described above are considered most appropriate and effective for the use in closing a tissue opening, in particular in fetoscopy. The needle guides accommodating the needles should not impede the freedom of movement of the needles.

The elongate shaft may comprise at least three needle guides, optionally at least four needle guides.

The exit openings may be spaced at least 3 mm, optionally at least 8 mm in the proximal direction from a proximally facing side of the support structure that is configured to be pressed against the tissue from within the body cavity (e.g. against the second tissue layer) when the support structure is in the second, expanded configuration. The exit openings may be located proximal of a most proximal position at which the support structure coupled (optionally movably coupled, such as hingedly coupled) to the elongate shaft, optionally proximal from a most proximal position at which the support structure is movably coupled to the elongate shaft.

Each of the needle guides may have a first portion and a second portion. The second portion may extend obliquely to the longitudinal axis. The first portion may be substantially parallel to the longitudinal axis. The second portion may form a distal portion of the respective needle guide. Additionally, each of the needle guides may comprise a curved segment, optionally wherein the curved segment is located between the first portion and the second portion and/or wherein the second portion is curved. The second portion may extend at least partially around the longitudinal axis. Furthermore, each of the needle guides may be configured such that the trajectory along which the respective needle extends from the exit opening extends at an angle to the longitudinal axis, optionally wherein the angle is at most 50°, optionally at most 30° and/or wherein the angle is at least 5°, optionally at least 10°.

The oblique extension of the needle guides may determine the trajectories of the needles from the exit openings to the connectors on the support structure. The oblique design may also determine the distance between two opposing needles when the needles reach their respective connector, which in turn defines the stich pattern and/or the size of tissue opening that may be closed.

The elongate shaft may comprise at least three exit openings, optionally at least four exit openings, optionally wherein the exit openings are spaced around a periphery of the elongate shaft. The exit openings may be spaced at regular intervals around the periphery of the elongate shaft.

The exit openings are optionally located along a peripheral side surface of the elongate shaft. Alternatively, the exit openings may be located at a distally facing surface of the elongate shaft. e.g. at a distally facing surface of the shaft provided by a reduction of the shaft's diameter.

Optionally, the exit openings are located distal from a first position at which the pushing member and/or the guide member is movably coupled to the elongate shaft, optionally distal from a most proximal position at which the pushing member and/or the guide member is movably coupled to the elongate shaft. Alternatively or additionally, the exit openings may be located proximal from a second position at which the pushing member is movably coupled to the elongate shaft, optionally proximal from a most distal position at which the pushing member and/or the guide member is movably coupled to the elongate shaft.

Each needle guide may have an entry opening at its proximal end. Optionally, the elongate shaft comprises two or more entry openings, optionally four entry openings. The entry openings may be located along an outer side surface of the elongate shaft. The needles may be pre-mounted in their respective needle guides. The entry openings allow for an easier mounting and adjustment of the needles within the needle guides of the elongate shaft.

The support structure in the first, contracted configuration may be configured to be inserted through the tissue opening into the body cavity. For this purpose, the support structure in the first, contracted configuration may be configured to not radially extend beyond an outer diameter of the elongate shaft and/or the support structure in the first, contracted configuration may have a diameter of 10 mm or less, optionally 5 mm or less.

The support structure in the second, expanded configuration may be configured to be pressed against the second tissue layer, optionally from within the cavity in a proximal direction, optionally by pulling the elongate shaft in the proximal direction. For this purpose, the support structure in the second, expanded configuration may extend beyond the outer diameter of the elongate shaft and/or the support structure in the second, expanded configuration may have a diameter of at least 5 mm, optionally at least 8 mm. The support structure in the second, expanded configuration may be configured such that the at least one first connector and the at least one second connector may be disposed on opposite sides of and/or around the tissue opening in the body cavity. Optionally, the support structure is configured to switch between the first, contracted configuration and the second, expanded configuration by pushing and pulling the elongate shaft along the longitudinal axis, respectively. In this manner, the device can be easily inserted through the tissue opening and deployed within the body cavity of the tissue to stably press against the tissue, e.g. against the second tissue layer, from within the cavity.

The device may further comprise at least one first actuation member extending along the elongate shaft, optionally wherein the first actuation member is a wire, a rod, a tube or a sleeve, the first actuation member being movable along the longitudinal axis, wherein the support structure is coupled to the first actuation member, optionally to a distal end thereof. Optionally, the support structure is moved to the contracted configuration by pushing the first actuation member in the distal direction with respect to the elongate shaft. Optionally, the support structure is moved to the expanded configuration by pulling the first actuation member in the proximal direction with respect to the elongate shaft. Alternatively, the support structure may be moved to the contracted configuration by pulling the first actuation member in the distal direction with respect to the elongate shaft and to the expanded configuration by pushing the first actuation member in the proximal direction with respect to the elongate shaft. Such construction with a first actuation member provides for a reliable and space-saving arrangement.

The support structure may be coupled to the first actuation member via at least one hinge. The longitudinal position of the hinge along the support structure may be fixed. The hinge may allow the support structure to expand.

The support structure may comprise a membrane cover. The membrane cover may prevent a portion of the tissue of being caught by the support structure, e.g., when the support structure moves from the expanded configuration back to the contracted configuration.

The support structure may comprise one or more support arms (optionally, a plurality of support arms) and/or one or more inflatable members. When using an inflatable member, the support structure may be moved from the collapsed configuration to the expanded configuration by inflating the one or more inflatable members.

According to a presently preferred configuration, the support structure comprises at least one support arm, optionally a plurality of support arms such as two, at least three, four or at least four support arms. Optionally, one or more pairs of the support arms are configured to expand on diametrically opposite sides of the elongate shaft.

Optionally, a first end of each support arm is movably connected to one of the elongate shaft and the first actuation member, optionally by a first hinge. The support structure may further comprise a plurality of support links, optionally two, at least three, four or at least four support links. Optionally, each of the support arms is connected to a respective support link by a movable joint, optionally by a second hinge. A second end of each of the support arms may be connected to a first end of the respective support link by the movable joint. A second end of the respective support link may be movably connected to the other one of the elongate shaft and the first actuation member, optionally by a third hinge. Each of the support arms and/or each of the support links in the first, contracted configuration may be substantially parallel to the longitudinal axis. Each of the support arms in the second, expanded configuration may be substantially perpendicular to the longitudinal axis. Each of the support links in the second, expanded configuration may be oblique to the longitudinal axis.

The support structure and its components may be produced using one or more additive manufacturing technologies.

The deployment of the support structure as described above using the support arms and the support links is a design that provides its mechanical stability. The connection by the joint structure between the support arm ant the support link is a simplistic mechanical design to realise the movement between a contracted configuration aligning with the longitudinal axis of the elongate shaft to an expanded configuration.

Each of the support arms may comprise a retainer for releasably retaining a respective one of the at least one first connector and the at least one second connector therein. Optionally each support arm comprises a release opening or slot for releasing the suture from the support arm. As an alternative to a retainer in the support arm, a holder may be placed in the support link.

Each retainer may be positioned at least 2 mm, optionally at least 5 mm, radially away from the longitudinal axis when the support structure is in the second, expanded configuration. The retainers may be configured to release the connector retained therein when a pushing or pulling force on the connector exceeds a predetermined threshold. For example, at least one retainer, optionally the retainer of the first connector, may be configured to release the connector retained therein when a distal pushing force applied on the connector by a respective needle exceeds a predetermined threshold. Optionally, at least another retainer, optionally the retainer of the second connector, is configured to release the connector retained therein when a proximal pulling force applied on the connector by the respective needle exceeds a predetermined threshold. Alternatively, the retainers of the first and second connectors may be configured to release the connector retained therein when a proximal pulling force applied by the respective needle exceeds a predetermined threshold. In this manner, different suturing concepts may be realized, as discussed in more detail below.

The retainers may temporarily be held by the support structure at their desired positions, while allowing the connectors to be released if the user and/or the device exerts a predetermined force or more.

One or more of the retainers may be surrounded by a funnel-shaped guiding surface configured to guide the respective needle into the respective connector. Such guiding surface may account minor deviations of the needle from its intended trajectory, which is particularly important in view of the small needle diameters discussed herein.

The shaft may be provided with one or more pockets at its distal end. The one or more pockets may be configured for receiving the support structure, in particular one or more of the support links, when the device is in the first, contracted configuration. As such, the elongate shaft may be configured to accommodate the support links in the contracted configuration.

The device may further comprise at least one first suture, thread or wire that is coupled to the first and second connectors. The at least one first suture, thread or wire may have a diameter smaller than 0.6 mm, optionally a diameter smaller than 0.4 mm, optionally a diameter smaller than 0.25 mm.

According to a first configuration, the at least one first suture, thread or wire is configured to be withdrawn from the tissue during use of the device. The first suture may also be referred to as a transfer suture in this case. Such transfer suture may be employed for pulling another suture, thread or wire from a first one of the first and second receivers to the other of the first and second receivers. Such transfer suture may be relatively short, e.g. 50 mm or less, optionally 30 mm or less, more optionally 15 mm or less.

Alternatively, a length of the first suture, thread or wire may be stored in a lumen, cavity and/or cartridge of the device. The length of the first suture may be at least 60 mm, optionally at least 400 mm, in this case, e.g. for fetoscopy applications. The length may be longer when closing other tissue openings. The at least one suture, thread or wire may be configured to remain in the tissue after the device is withdrawn. Alternatively, the suture, thread or wire may be used to pull another suture which remains in the body through the tissue.

The lumen may be a lumen of the elongate shaft and/or a lumen of the first actuation member. The lumen may extend to at least one distal opening through which the first suture, thread or wire enters into the lumen. The length of the first suture, thread or wire may be stored in the lumen as at least one loop. The first suture, thread or wire may extend through the lumen along the longitudinal axis.

The cavity or cartridge may be arranged at the distal end of the elongate shaft. Such cavity or cartridge may comprise a spool onto which at least part of the length of the first suture, thread or wire is wound.

The devices disclosed therein may comprise two first sutures as described above. The two first sutures may be attached to each other at a crossing point.

Any of the sutures and threads mentioned herein may be made from or comprise a polymeric material (including poly lactic acid, poly glycolic acid, polydioxanone. Polycaprolactone, polyhydroxybutyrates, copolymers or blends thereof), silk, catgut, or others, as known in the art. The sutures and threads may be a monofilament or braided. Any of the sutures and threads mentioned herein may be made from a resorbable material. Any of the sutures and threads mentioned herein may be provided with a coating. Such coating may have antibacterial properties and/or provide for easier gliding. The sutures or threads mentioned herein may be elastic and/or plastically deformable. The sutures or threads mentioned herein may be provided with a glue for containing liquid within the body cavity, one or more growth factors, and/or gelatine.

The at least one suture may further comprise at least one washer, optionally at least two or at least four washers, configured to remain in the tissue and to cover the stitching holes penetrated by the first and second needles, optionally wherein the at least one washer is pre-arranged on the at least one suture. The one or more washers are optionally arranged on the suture in such manner that they are located within the body cavity after the tissue opening is closed. In particular, the one or more washers may be configured to be located within the body cavity in abutment against the tissue, in particular in abutment against the second tissue layer. The washer may be resorbable.

The one or more washers may have a diameter of less than 3 mm, optionally less than 2 mm. The one or more washers may have a thickness of less than 2 mm, optionally less than 1 mm. Alternatively or additionally to the one or more washers, the at least one suture may comprise at least one patch that is configured to remain in the body cavity and overlap with the closed tissue opening from within the cavity. Optionally, the at least one patch is elastic and/or resorbable.

The fetal membrane is very delicate and pulling the suture through the tissue or creating a suture knot with too much force may lead to cutting into the tissue. The stitching holes in the second tissue layer are vulnerable areas within the tissue. Thus, placing one washer each approximately with a diameter of, for example, 1.5 mm and a thickness of 0.5 mm below the suture at each stitching holes could minimize the risk of tissue cutting. Such washer could also help to press the foetal membrane towards the uterus, whereby it is believed (without wanting to be bound by theory) that resistance of the foetal membrane to cutting may be increased.

The support structure and/or a distal tip of the device may comprise at least one groove or channel configured to releasably retain and/or guide the first suture, thread or wire therein. The groove or channel may comprise a first width in cross section, and the support structure may further comprise a slot for releasing the first suture form the groove or channel, wherein the slot comprises a second width in cross section that is less than the first width. The support structure may comprise a plurality of grooves or channels that are spaced apart from each other.

The one or more grooves or channels may be provided along one or more of the support arms and/or support links, optionally on a side of the respective support arms and/or support links that faces in the distal direction when the support structure is in the second, expanded configuration. The one or more grooves or channels may at least partially extend in a structure protruding from the respective support arms and/or support links.

The first suture may be pre-mounted in the groove or channel so that it does not interfere with deployment of the support structure. The support structure may be configured to hold the first suture taut in the groove or channel when in the first, contracted configuration and/or when in the second, expanded configuration. For example, the length of the suture may be similar to the length of the suture's path in the at least one groove or channel. Alternative configurations are also envisaged. For example, release of the first suture from the groove or channel could be inhibited until a respective release mechanism is actuated, which allows the suture to slip out of the groove or channel. The release mechanism could be configured to move apart two portions of a respective support arm and/or a respective support link forming the groove or channel, e.g. to open the groove or channel and/or increase the width of the slot.

The at least one first needle and the at least one second needle may be configured to move separately.

Optionally, the first needle and the second needle have a sharp distal end.

The at least one first needle and/or the at least one second needle may be made from a metallic material, optionally nitinol, stainless steel or titanium. Furthermore, the first needle and the second needle may have an outer diameter smaller than 2 mm, optionally an outer diameter smaller than 1 mm, optionally an outer diameter smaller than 0.5 mm. Such size dimensions are considered most appropriate and effective for the penetration of the fetal membrane.

According to a first configuration, the at least one second needle has a releasable tip. A second suture, thread or wire may be coupled to the releasable tip, optionally wherein the second suture, thread or wire may extend at least partially through the second needle lumen and/or the second needle guide. The second suture, thread or wire may be configured to be pulled through the at least one second needle and/or the second suture, thread or wire may be configured to be pulled through the elongate shaft. The second suture, thread or wire may extend along the elongate shaft towards the proximal end of the elongate shaft, optionally wherein the second suture, thread or wire remains accessible to a user outside a body of a patient being treated for connecting a further suture thereto. The at least one second suture, thread or wire may have a diameter smaller than 0.5 mm, optionally a diameter smaller than 0.35 mm, optionally a diameter smaller than 0.2 mm.

Optionally, the releasable tip is configured to be coupled with and retained by the second connector, optionally via a form fit or a press fit coupling. The releasable tip may comprise an undercut and/or a barbed hook for coupling with the second connector. The first needle may be configured to retract the first and second connectors in a proximal direction through the needle guide of the first needle. In other words, the first needle may be used for retrieving the first connector and the second connector in the proximal direction. The first connector may be coupled to the second connector via the first suture mentioned above. The second connector may be drawn proximally by the first needle through the needle guide of the first needle.

In this first configuration, the at least one second needle may be a hollow needle comprising a second needle lumen extending therethrough. The second suture may extend through the needle lumen.

The at least one first needle in this configuration may be a solid needle, i.e. a needle that is devoid of a needle lumen extending therethrough. Alternatively, the at least one first needle may be a hollow needle comprising a needle lumen extending therethrough. In this case, the first and/or second needle may be configured to inject fluids therethrough into the tissue, e.g. one or more growth factors or a glue. Since the stitching holes can be vulnerable areas that can possibly tear in the closure of the tissue opening, additionally injecting fluids, e.g., glue or growth factor, can stabilize the tissue.

According to a second configuration, the at least one first needle may be configured to retract the first connector in a proximal direction through the needle guide of said first needle, and the at least one second needle may be configured to retract the second connector in a proximal direction through the needle guide of said second needle. In this case, the first needle and/or the second needle may be solid needles that are devoid of a needle lumen extending therethrough. However, the first needle and/or the second needle may also be hollow needles comprising a needle lumen extending therethrough (e.g., for injecting fluids therethrough into the tissue, such as one or more growth factors or a glue).

Any of the above-mentioned first and second configurations may comprise at least two first needles and at least two second needles. Four needles are advantageous for providing a cross-stitching with two sutures. A cross-stitching is believed to be beneficial for ensuring an adequate closure of the tissue opening in view of the small dimensions of the opening, e.g. in fetoscopy.

The device may further comprise at least one second actuation member. The second actuation member may extend along the elongate shaft, the second actuation member being movable along the longitudinal axis between a first position and a second position, optionally wherein the first position is a distally advanced position and the second position is a proximally retracted position. The pushing member may be moved to the contracted configuration by moving the second actuation member to the first position and to the expanded configuration by moving the second actuation member to the second position, or vice versa. The second actuation member may be a wire, a rod, or a tube or sleeve.

The at least one pushing member in the contracted configuration optionally does not radially extend beyond an outer diameter of the elongate shaft.

When expanded, the at least one pushing member may be configured to lift the first tissue layer away from the second tissue layer in a proximal direction and/or to push the first tissue layer away from the device perpendicularly to the longitudinal axis in a radially outward direction. The directions of the expanding motion of the pushing members allow the pushing member to lift one or more tissue layer, e.g., fascia, in a soft and safe manner without damaging the tissue layers.

The at least one pushing member may be expandable together with the support structure. For example, the at least one pushing member may be coupled to the first actuation member. Alternatively, the at least one pushing member may be expandable independently of the support structure, e.g. by coupling it to the second actuation member.

The device, optionally a handle thereof, may be configured such that the at least one pushing member can only be moved to its expanded configuration once the support structure is moved to its expanded configuration.

It is preferred that the at least one pushing member is located at least 2 mm away, optionally at least 5 mm away, from the distal end of the elongate shaft and/or the at least one pushing member is located at most 100 mm away, optionally at most 20 mm away, from the distal end of the elongate shaft. These distances are believed to be helpful for pushing the relevant tissue, in particular fascia, out of the trajectory of the needles.

The at least one pushing member may comprise a membrane cover. Optionally, the membrane cover covers the pushing member from the proximal direction.

By moving the first tissue layer out of the trajectories of the needles, the tissue opening of the second tissue layer may be closed. Meanwhile, an attachment of the first tissue layer to said second tissue layer may be avoided. This is believed to be helpful in cases where the first and second tissue layers move relatively to each other over time, e.g., expansion of the womb during pregnancy of a patient.

The at least one pushing member may comprise a plurality of flaps, optionally two or at least four flaps. The at least one pushing member may be rotatably coupled to one of the elongate shaft, the first actuation member and a second actuation member. The at least one pushing member may be coupled to one of the elongate shaft, the first actuation member and a second actuation member, via at least one hinge.

A first end of each of the flaps may be movably connected to one of the elongate shaft, the first actuation member and a second actuation member, optionally by a hinge. The mechanism of lifting one or more tissue layer by a rotating motion reduces the risk of damaging the tissue layers.

The at least one pushing member may further comprise a plurality of pushing member links, optionally two or at least four pushing member links, optionally at least one pushing member link for each flap. Each of the flaps may be connected to a respective pushing member link by a movable joint, optionally a hinge.

More specifically, a second end of each of the flaps may be connected to a first end of a respective pushing member link by the movable joint. Optionally, a second end of the respective pushing member link is movably connected to one of the first actuation member, a second actuation member or the elongate shaft, optionally by a hinge. In particular, the second end of the respective pushing member link optionally is movably connected to another one of the first actuation member, a second actuation member or the elongate shaft than the respective flap. In this manner, the points at which the flap and the link are connected to the shaft or the first/second actuation member may be moved towards each other and/or away from each other in order to expand and contract the pushing member, respectively. Coupling the flaps or the links to the second actuation member via a hinge allows for an advantageous and space-saving design of the device.

According to a first alternative configuration, the second actuation member may be configured to maintain the pushing member in the contracted configuration by at least partially covering the flaps, e.g. when the second actuation member is in the first position. The second actuation member may allow the flaps to move to the expanded configuration when in the second position. A second actuation member in the form of a sleeve may be advantageous for this purpose. The flaps may be biased towards a radially outward, expanded configuration. For this purpose, the flaps may be made from an elastic material (e.g., nitinol) and/or the flaps may be connected to the elongate shaft by a spring hinge.

According to a second alternative configuration, which may be combined with the first alternative configuration, the second actuation member is configured to move the flaps radially outward when in the second position. For this purpose, a portion of the second actuation member may be disposed between the flaps and the elongate shaft when the second actuation member is in the second position. In this case, the flaps may be biased radially inwards. The second actuation member may be provided as a sleeve.

According to a third alternative configuration, each of the flaps is coupled to the second actuation member, or to a respective second actuation member, at a position that is eccentric to an axis around which the respective flap rotates when moving the pushing member from the contracted configuration to the expanded configuration.

The at least one pushing member, optionally the at least one flap, may comprise at least one marker for determining the configuration of the pushing member in a medical imaging procedure, optionally wherein the marker is an ultrasound marker and/or a radiopaque material. The at least one pushing member, optionally the at least one flap, may be made from an ultrasound visible material and/or a radiopaque material. Optionally, the support structure, optionally the at least one support arm, may be made from an ultrasound visible material and/or a radiopaque material. Ultrasound visibility may be achieved, for example, by using porous polymers (e.g. foams), providing gas bubbles on inner or outer surfaces of the flaps (as discussed, e.g., in WO 2012/148265 A1, which is herein incorporated by reference in its entirety), surface roughening (e.g., by means of polishing, sand blasting or electric discharge machining), or by introducing contrast enhancing particles into the material (as discussed, e.g., in EP 1 155 418 B1, which is herein incorporated by reference in its entirety).

It should be noted that any intervention in accordance with the methods of the present invention may be performed under ultrasound guidance. In particular, such ultrasound guidance may be provided during the expansion and/or retraction of the support member, during the expansion of the at least one pushing member, and/or when advancing the needles to the expanded support structure. Optionally, the fetoscopy can be performed using an ultrasound guidance throughout the operation or at least during the expansion of the at least one pushing member and when the needles are advanced and connected to the expanded support structure.

The use of an ultrasound visible material provides additional visibility and certainty whether the first tissue layer has been sufficiently pushed away before the advancement of the needles.

Alternatively or additionally to the above-mentioned flaps and/or links, the at least one pushing member may be provided as or may comprise an inflatable structure, for example an inflatable balloon. Such inflatable structure may be used, e.g., to expand the flaps (by inflating the inflatable structure, for example with a gas or a liquid).

Optionally, the at least one expandable guide member in the contracted configuration does not radially extend beyond an outer diameter of the elongate shaft. The at least one expandable guide member may comprise at least one guide opening, which in the expanded configuration overlaps with the first or second trajectory, optionally at least one first guide opening that overlaps with the first trajectory and at least one second guide opening that overlaps with the second trajectory. The guide member may overlap with the respective trajectory at a respective guiding position. The guiding position may be spaced from the exit opening of the respective needle radially and/or along the longitudinal axis.

Optionally, the at least one guide opening is positioned proximally of the second tissue layer when the guide member is expanded.

The at least one guide opening may be located at least 2 mm away, optionally at least 3 mm away, from the longitudinal axis. The at least one guide opening may be located at most 8 mm away, optionally at most 5 mm away, from the longitudinal axis.

Alternatively or additionally, the at least one guide opening may be located at least 1.5 mm away, optionally at least 3 mm away, from the distal end of the elongate shaft. The at least one guide opening may be located at most 80 mm away, optionally at most 15 mm away, from the distal end of the elongate shaft.

The guide opening may be surrounded by a funnel-shaped guiding surface configured to guide a respective needle into the guide opening.

The at least one guide opening may comprise a release opening or release slot for releasing the suture from the guide opening, optionally wherein the release opening or release slot extends to a periphery of the guide member and is open at the periphery of the guide member, optionally wherein the release opening or release slot extends from the guide opening in a radially inward direction.

Without the expandable guide member, the relatively long trajectories of the needles can become a factor that may adversely affect the accuracy of the operation. The expandable guide member as additional guidance in-between can correct the trajectories of the needles between the exit openings and the connectors.

Optionally, the at least one guide opening has a width and/or diameter smaller than 2 mm, optionally smaller than 1 mm, optionally smaller than 0.5 mm. It is preferred that the at least one guide opening has a length smaller than 2 mm, optionally smaller than 0.5 mm along the first and/or second trajectories in the expanded configuration. Such dimensions of the guide openings are considered most appropriate and effective for the guidance of the needles along their trajectories in terms of achieving the necessary accuracy, but also within an allowable tolerance range, e.g. for fetoscopy applications.

The at least one expandable guide member may comprise a membrane cover.

Optionally, the at least one guide member is connected to the elongate shaft by at least one hinge, optionally wherein the at least one guide member comprises a plurality of arms, each of which is hinged to the elongate shaft.

The at least one expandable guide member may be formed by one or more of the plurality of pushing member links.

According to a third aspect of the present invention, a device for closing a tissue opening in a tissue with at least one suture is disclosed. The tissue extends at least partially around a body cavity and optionally comprises at least first and second tissue layers, the second tissue layer extending between the first tissue layer and the body cavity. The first tissue layer may be a fascia. The second tissue layer may be a uterus.

According to this third aspect, the device comprises an elongate shaft having a proximal end, a distal end and extending along a longitudinal axis, the elongate shaft configured to be inserted into the tissue opening, the elongate shaft comprising a plurality of needle guides, each needle guide having an exit opening at its distal end; a support structure at the distal end of the elongate shaft configured to move between a first, contracted configuration and a second, expanded configuration, the support structure comprising at least one support arm, the support structure being configured to be expanded in the body cavity; at least one first needle and at least one second needle; at least one first connector and at least one second connector releasably coupled to the support structure such that the first and second connectors are disposed on opposite sides of and/or around the tissue opening in the body cavity in the second, expanded configuration, the first connector being configured to couple with a distal end of the first needle and the second connector being configured to couple with a releasable tip of the second needle. Each of the needles is configured to be translated along a respective one of the needle guides. The first needle is configured to be advanced out of the exit opening of the respective needle guide and to penetrate through the second tissue layer along a first trajectory, the first trajectory extending from the exit opening through the second tissue layer obliquely to the longitudinal axis to the first connector, and the second needle is configured to be advanced out of the exit opening and to penetrate through the second tissue layer along a second trajectory, the second trajectory extending from the exit opening through the second tissue layer obliquely to the longitudinal axis to the second connector. The device also comprises at least one auxiliary suture, thread or wire coupled to the at least one first connector and the at least one second connector, and at least one further suture, thread or wire, the at least one further suture, thread or wire being coupled to the releasable tip and extending along the elongate shaft and/or along the second needle.

The further suture, thread or wire may be coupled to the second connector via the releasable tip. The first connector may be coupled to the first needle. By pulling the first needle in the proximal direction, the first connector, the auxiliary suture, thread or wire, the second connector, and at least a portion of the further suture, thread or wire may be pulled through the needle guide of the first needle proximally. In this manner, the tissue opening may be closed.

According to a fourth aspect of the present invention, a device for closing a tissue opening in a tissue with at least one suture is disclosed. The tissue extends at least partially around a body cavity and optionally comprises at least first and second tissue layers, the second tissue layer extending between the first tissue layer and the body cavity. The first tissue layer may be a fascia. The second tissue layer may be a uterus.

The device comprises an elongate shaft having a proximal end, a distal end and extending along a longitudinal axis, the elongate shaft configured to be inserted into the tissue opening, the elongate shaft comprising a plurality of needle guides, each needle guide having an exit opening at its distal end; a support structure at the distal end of the elongate shaft configured to move between a first, contracted configuration and a second, expanded configuration, the support structure comprising at least one support arm, the support structure being configured to be expanded in the body cavity; at least one first needle and at least one second needle; at least one first connector and at least one second connector releasably coupled to the support structure such that the first and second connectors are disposed on opposite sides of and/or around the tissue opening in the body cavity in the second, expanded configuration, the first connector being configured to couple with a distal end of the first needle and the second connector being configured to couple with a distal end of the second needle. Each of the needles is configured to be translated along a respective one of the needle guides. The first needle is configured to be advanced out of the exit opening of the respective needle guide and to penetrate through the second tissue layer along a first trajectory, the first trajectory extending from the exit opening through the second tissue layer obliquely to the longitudinal axis to the first connector, and the second needle is configured to be advanced out of the exit opening and to penetrate through the second tissue layer along a second trajectory, the second trajectory extending from the exit opening through the second tissue layer obliquely to the longitudinal axis to the second connector. The device also comprises at least one suture, thread or wire coupled to the at least one first connector and the at least one second connector. At least a portion of the at least one suture, thread or wire optionally is stored within a lumen, a cavity or a cartridge of the device, as described hereinabove.

By using one suture that is connected to the at least one first connector and the at least one second connector, the needles can be both solid needles, which merely retrieve the suture upwards in the proximal direction by connecting to the connectors. This may provide for a simpler overall design of the device.

It is noted that the third and fourth aspects of the present invention may further comprise any of the features as described above in relation to the first and second aspects of the present invention.

The invention does also encompass a corresponding method for suturing an opening in a tissue using the device according to any of the preceding aspects.

The present summary is provided only by way of example and not limitation. Other aspects of the present invention will be appreciated in view of the entirety of the present disclosure, including the entire text, claims, and accompanying figures.

BRIEF DESCRIPTION OF THE DRAWINGS

The invention will be described in more detail with reference to the figures below. These figures disclose embodiments of the invention for illustrational purposes only. In particular, the disclosure provided by the figures is not meant to limit the scope of protection conferred by the invention.

DETAILED DESCRIPTION

As used herein, "proximal" means closest to the surgeon, while "distal" means farthest from the surgeon. In other words, "proximal" means farthest from the tissue opening, while "distal" means closest to the tissue opening and/or farthest within the body cavity.

Figure 1:
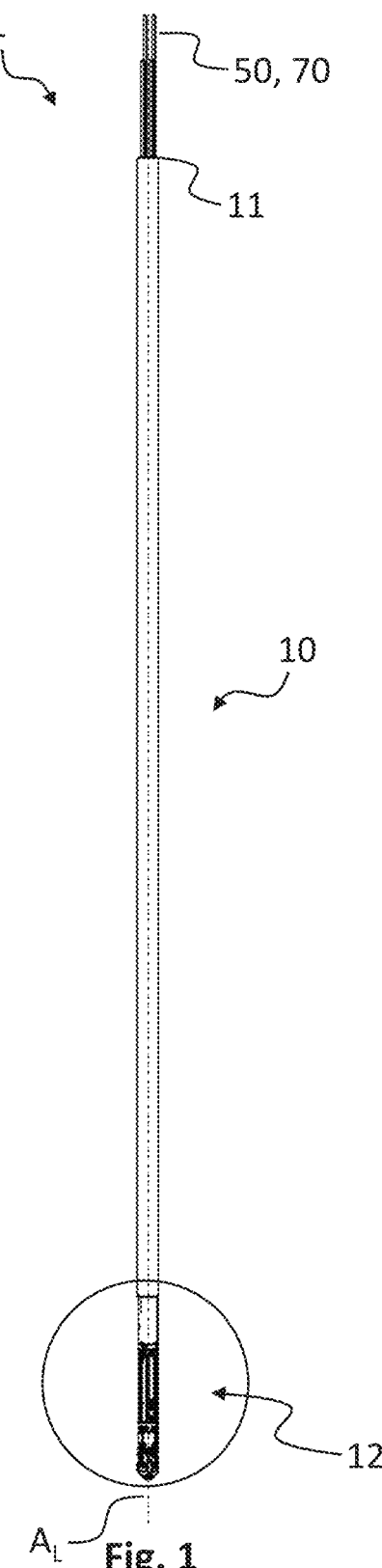
FIG. 1 is a schematic front view of a device for closing a tissue opening in accordance with an embodiment of the present invention.

FIG. 1 schematically illustrates a device 1 according to either one of the first aspect and second aspect of the present invention. The device 1 comprises an elongate shaft 10 having a proximal end 11, a distal end 12 and extending along a longitudinal axis $A_L$. The proximal end 11 comprises at least one suture 50, 70. The proximal end 11 comprises a handle (not illustrated) to be operated by the user. The distal end 12 is configured to be inserted into a body cavity 105 of a tissue 100 through a tissue opening 101 in a tissue 100.

FIGS. 2A-8B show details of the distal end 12 of the device 1, as indicated by the circled area in FIG. 1.

Figure 2A:
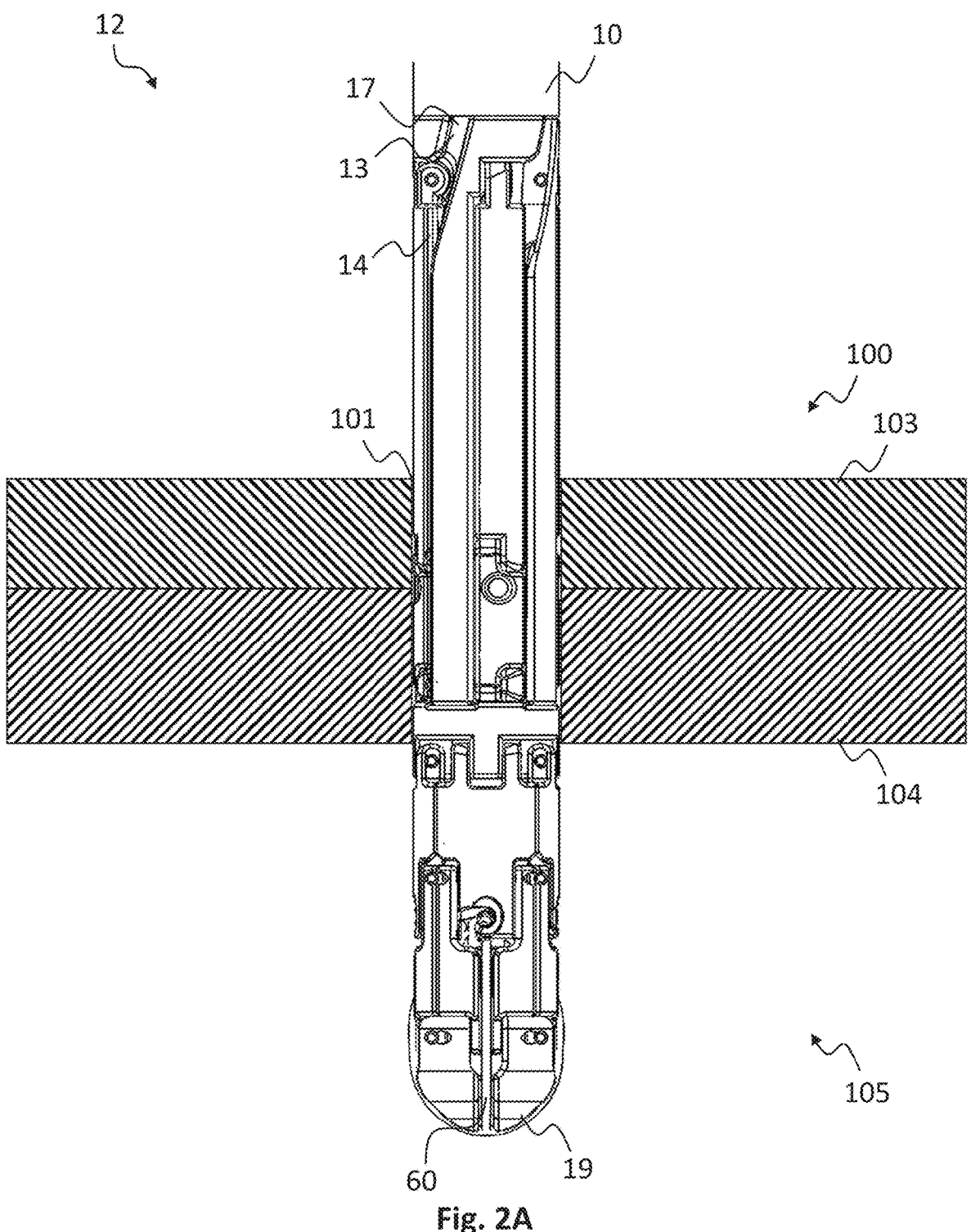
FIG. 2A-2C are schematic front views illustrating the device of FIG. 1 at its distal end being inserted into a tissue opening, shifting to the expanded configuration and deploying a first needle and a second needle.
Figure 2B:
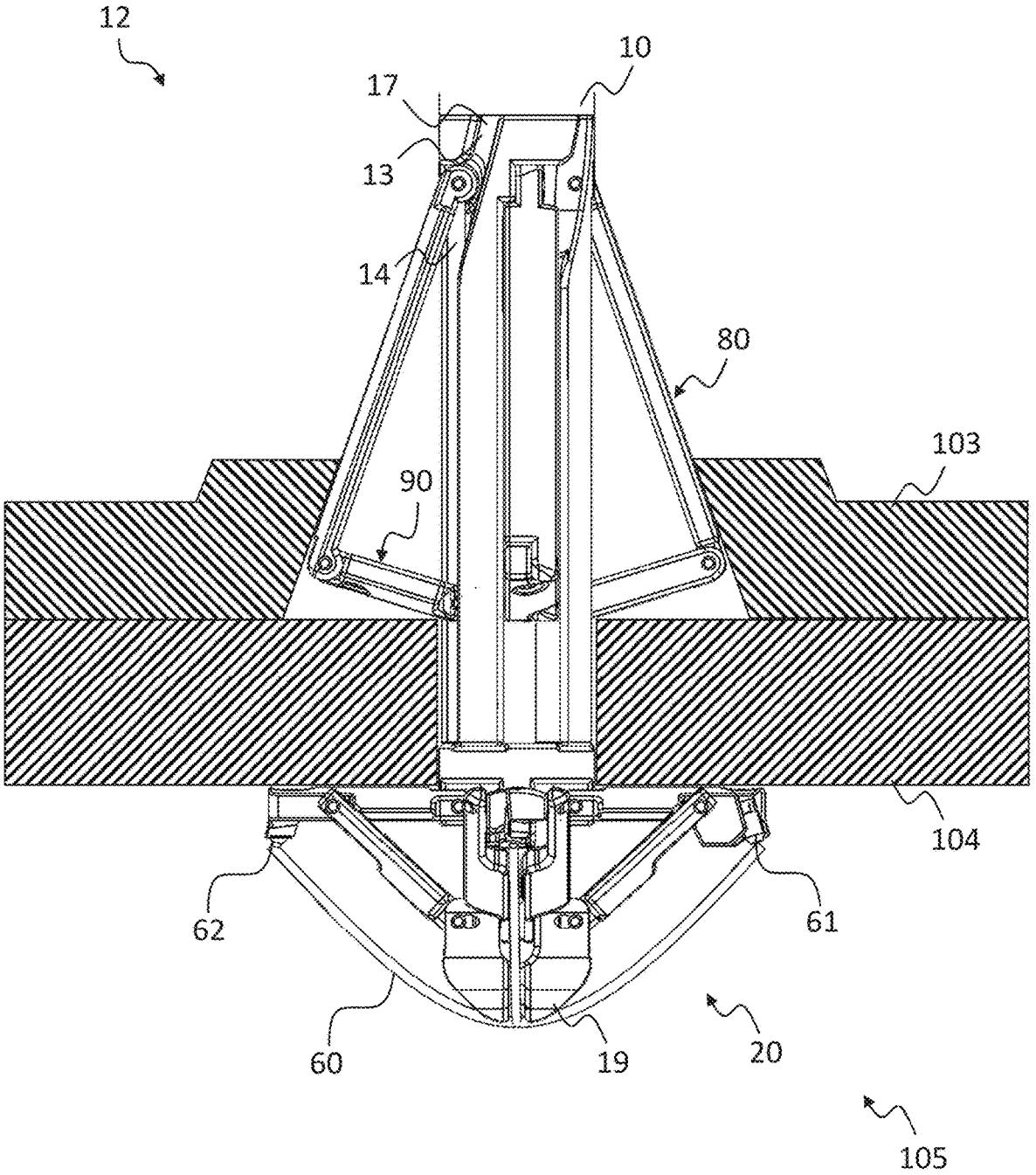
Figure 2C:
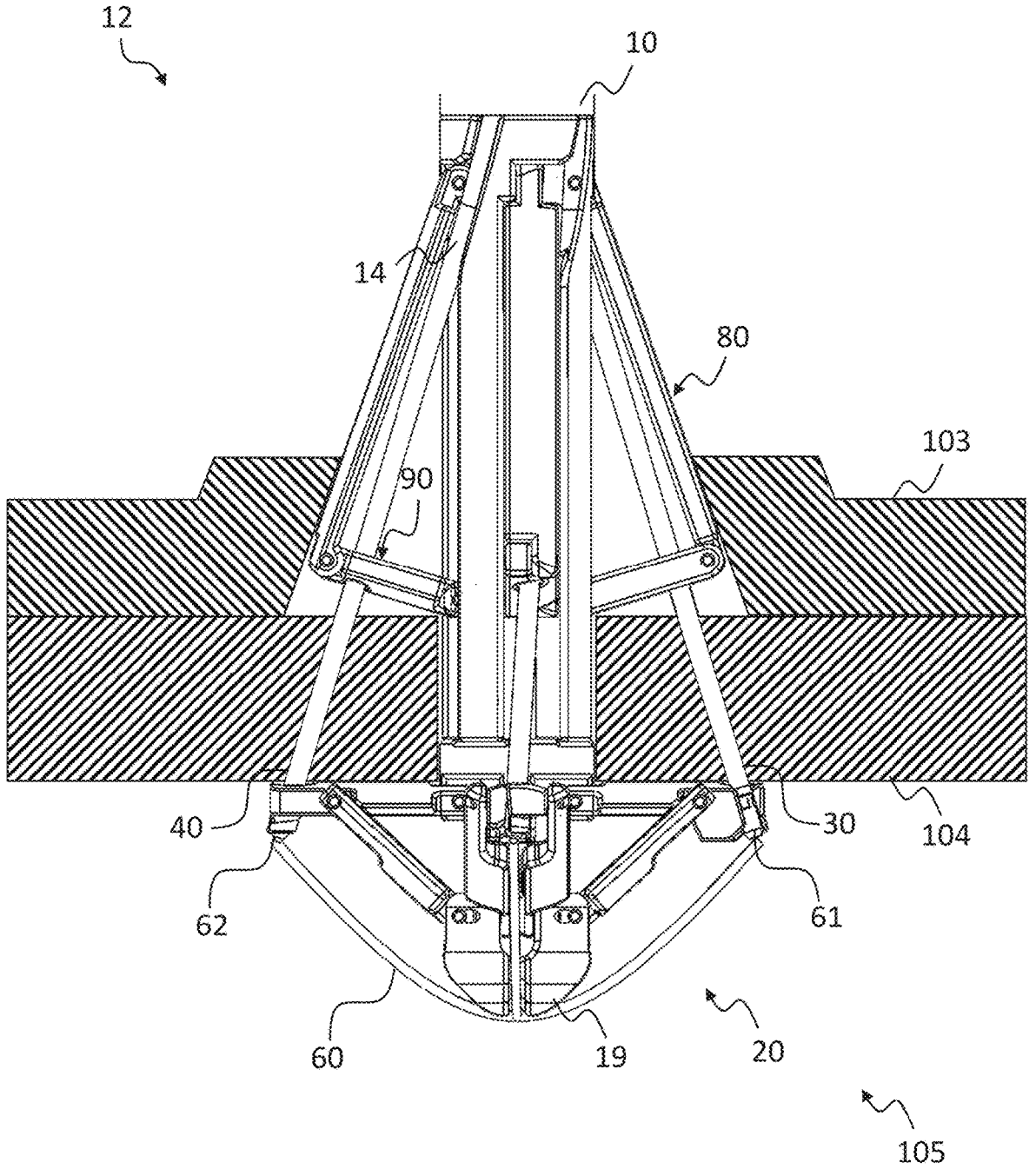

FIGS. 2A-2C schematically illustrate the device 1 being used for closing the tissue opening 101 in the tissue 100. The device 1 comprises an atraumatic distal tip 19.

After the main surgery or an endoscopic procedure, e.g., fetoscopy for a fetus, is completed, the related instruments are removed. A catheter (not illustrated) providing access to the tissue opening 101 may remain inserted in the tissue opening 101. FIG. 2A illustrates the device 1 after being inserted through the catheter, so that the distal end 12 of the device 1 protrudes into the body cavity 105.

In a next step as shown in FIG. 2B, a support structure 20 at the distal end 12 is shifted from a first, contracted configuration to a second, expanded configuration, e.g., by pulling an actuator. The support structure 20 is pulled proximally against a second tissue layer 104, which can be a uterus. The second tissue layer 104 extends between a first tissue layer 103 and the body cavity 105. The first tissue layer 103 may be fascia. As shown, the first tissue layer 103 can be lifted away from the second tissue layer 104 softly. The transition of the outer surface of the first tissue layer 103 is illustrated angular, which is rounder and more gradual in reality.

Simultaneously with or independently from the expansion of the support structure 20, an expandable pushing member 80 is deployed from a first, contracted configuration to a second, expanded configuration by using an actuator. The expandable pushing member 80 lifts and/or pushes the first tissue layer 103 that is located proximally from the second tissue layer 104 away from the trajectories of at least one first and second needles 30; 40 of the device 1. The first and second needles 30; 40 are then advanced out from exit openings 14 of the elongate shaft 10 through the second tissue layer 104 to respective first and second connectors 61; 62 located on the support structure 20, as shown FIG. 2C. The exit openings 14 are positioned at the distal end of needle guides 13 in the elongate shaft 10. The needle guides 13 have a first portion 16 and a second portion 17. The second portion 17 forms a distal portion of the respective needle guides 13 and extend obliquely to the longitudinal axis $A_L$ of the elongate shaft 10. As a result, the trajectories of the needles 30, 40 extend straight out of the exit openings 14 and obliquely to the longitudinal axis $A_L$ of the elongate shaft 10. On a side note, the first portion 16 of the needle guides 13 may or may not extend substantially parallel to the longitudinal axis $A_L$ of the elongate shaft 10 (see also FIG. 4A).

The device 1 further comprises at least one expandable guide member 90 that is configured to move between a contracted configuration and an expanded configuration to guide the needles 30; 40 along their respective trajectory. As shown, the expandable pushing members 80 and the expandable guide members 90 can be integrated into a single expandable structure.

Referring to FIG. 2C, the first and second needles 30; 40 extended out of the exit openings 14 puncture only through the second tissue layer 104 and reach their respective first and second connectors 61; 62 with accuracy. The first connector 61 and the second connector 62 are disposed on opposite sides of the tissue opening 101 in the body cavity 105.

A pre-mounted first suture 60 coupled to the connectors 61; 62 is configured to be coupled with a releasable tip 51 of the second needle 40 via the second connector 62. The releasable tip 51 is attached to a second suture 50 disposed inside the second needle 40. The first suture 60 is further configured to be coupled with the first needle 30 via the first connector 61. The first needle 30 can be used to pull the first connector 61, the first suture 60, the second connector 62, the releasable tip 51, and at least a portion of the second suture 50 proximally through the needle guide 13 of the first needle 30, such that the second suture 50 extends within the body cavity 105 from the puncture site of the first needle 30 to the puncture site of the second needle 40. In this context, reference to the second suture 50 shall also encompass a further suture that may be attached to a proximal end of said second suture 50 during the procedure.

The remainder of the second needle 40 may be retracted into its respective needle guide. The expandable pushing members 80 and the expandable guide members 90 may then be folded back to their contracted configuration.

After shifting the support structure 20 back to its contracted configuration, the device 1 may be removed from the tissue 100. The second suture 50 may then be removed from the device 1 by pulling the device 1 in the proximal direction and/or out of the patient's body. The ends of the second suture 50 extending proximally from the tissue 100 may be tied to a knot, and the tissue opening 101 may be closed.

FIGS. 3A-3H schematically illustrate the device 1 in further detail.

Figures 3A, 3B:
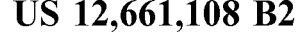
FIG. 3A-3H are schematic perspective views illustrating the device of FIG. 1 at its distal end during individual operational steps performed for the closure of a tissue opening.

In FIGS. 3A and 3B, a groove or channel 25 for releasably retaining the suture 60 is shown. As shown in FIG. 3A, portions of the groove or channel 25 may extend along the distal tip 19 of the device 1 and/or at least partially along the support structure 20. The groove 25A at the distal tip 19 is configured to retain the first suture 60 when in the first, contracted configuration and to release and guide the first suture 60 when in the second, expanded configuration.

In the expanded configuration of the support structure 20 as shown in FIG. 3B, the first and second connectors 61, 62 are retained on opposing support arms 21 in respective retainers 23 (see also FIG. 4B) of the support structure 20. Each first end of the four support arms 21 is movably connected to the elongate shaft 10 by a first hinge. The support arms 21 are connected at their second ends to respective support links 22 at their first ends by a second hinge. The support links 22 are each movably connected to a first actuation member 63 (see also FIG. 4B) at their second ends by a third hinge. The joint structure of the support structure 20 enables a movement from the first, contracted configuration, where the support arms 21 and the support links 22 are substantially parallel to the longitudinal axis $A_L$, to the second, expanded configuration, where the support arms 22 are substantially perpendicular to the longitudinal axis $A_L$ and the support links 22 are oblique to the longitudinal axis $A_L$. Furthermore, the support arms 21 retaining the first connectors 61 each comprise a protrusion with a groove 25B at its proximally facing side when in the second, expanded configuration that is configured to guide the first and second sutures 50; 60 later when the first needle 30 is pulled in the distal direction.

Figures 3C, 3D:
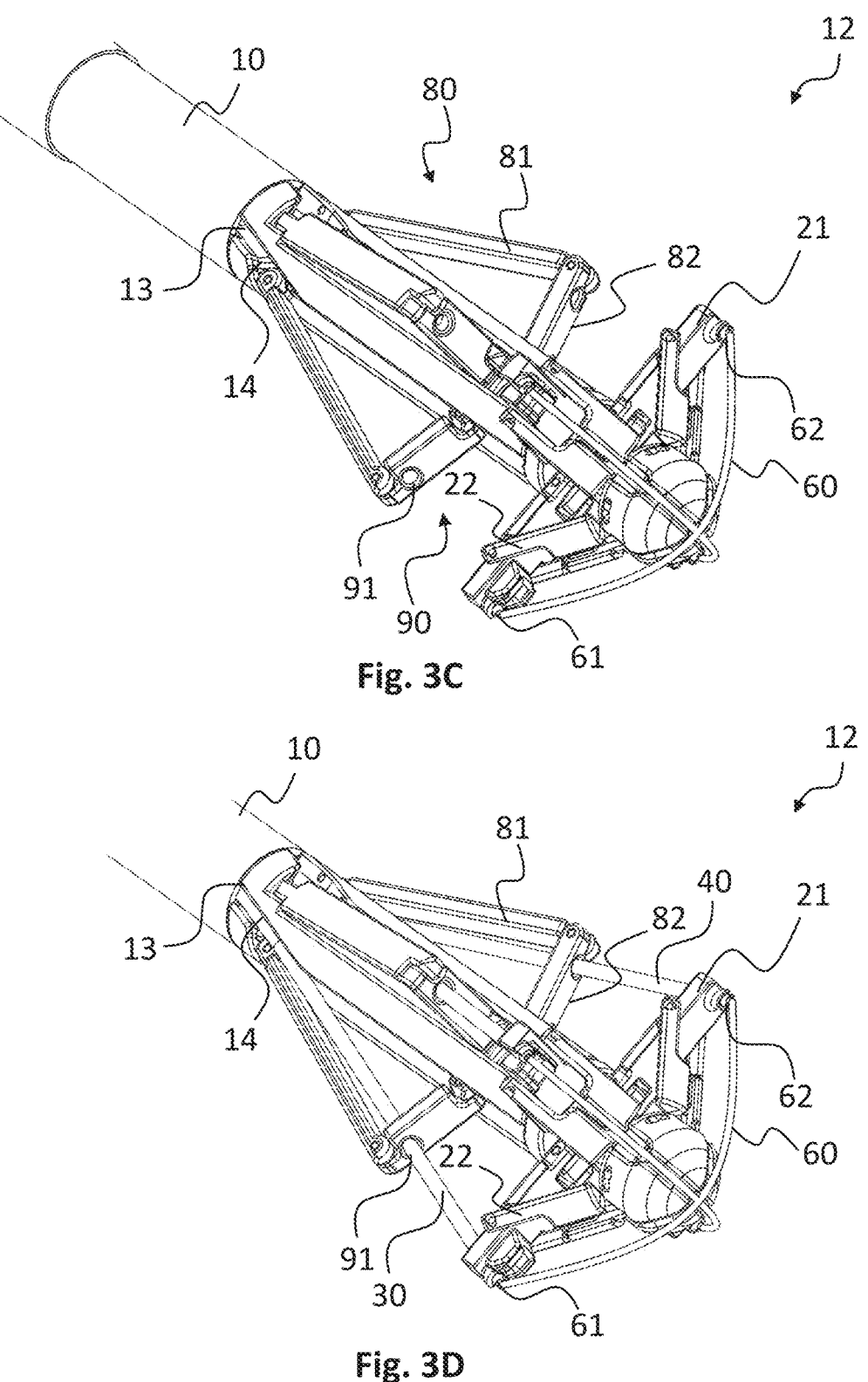

As shown in FIG. 3C, the expandable pushing member 80 having a plurality of pushing member flaps 81 and the expandable guide member 90 having at least one guide opening 91 are integrated into a single component. Each first end of the four pushing member flaps 81 of the expandable pushing member 80 is movably connected to the elongate shaft 10 by a first hinge. The pushing member flaps 81 are connected at their second ends to respective pushing member links 82, in particular to a first end of said links 82, by a second hinge. The pushing member links 82 are at the same time the expandable guide members 90 forming the guide opening 91 overlapping with the trajectories of the needles 30, 40. The pushing member links 82 are each movably connected to a second actuation member in form of a sleeve 83 (see also FIG. 4C), e.g. at their respective second end via a hinge.

FIG. 3D illustrates how the needles 30, 40 pass through the guide opening 91 of the respective expandable guide member 90. The first trajectory is formed by the first needle 30 extending from the exit opening 14 through the second tissue layer 104 obliquely to the longitudinal axis $A_L$ to the first connector 61 and the second trajectory is formed by the second needle 40 extending from the exit opening 14 on the opposing side of the elongate shaft 10 through the second tissue layer 104 obliquely to the longitudinal axis $A_L$ to the second connector 62.

Figures 3E, 3F:
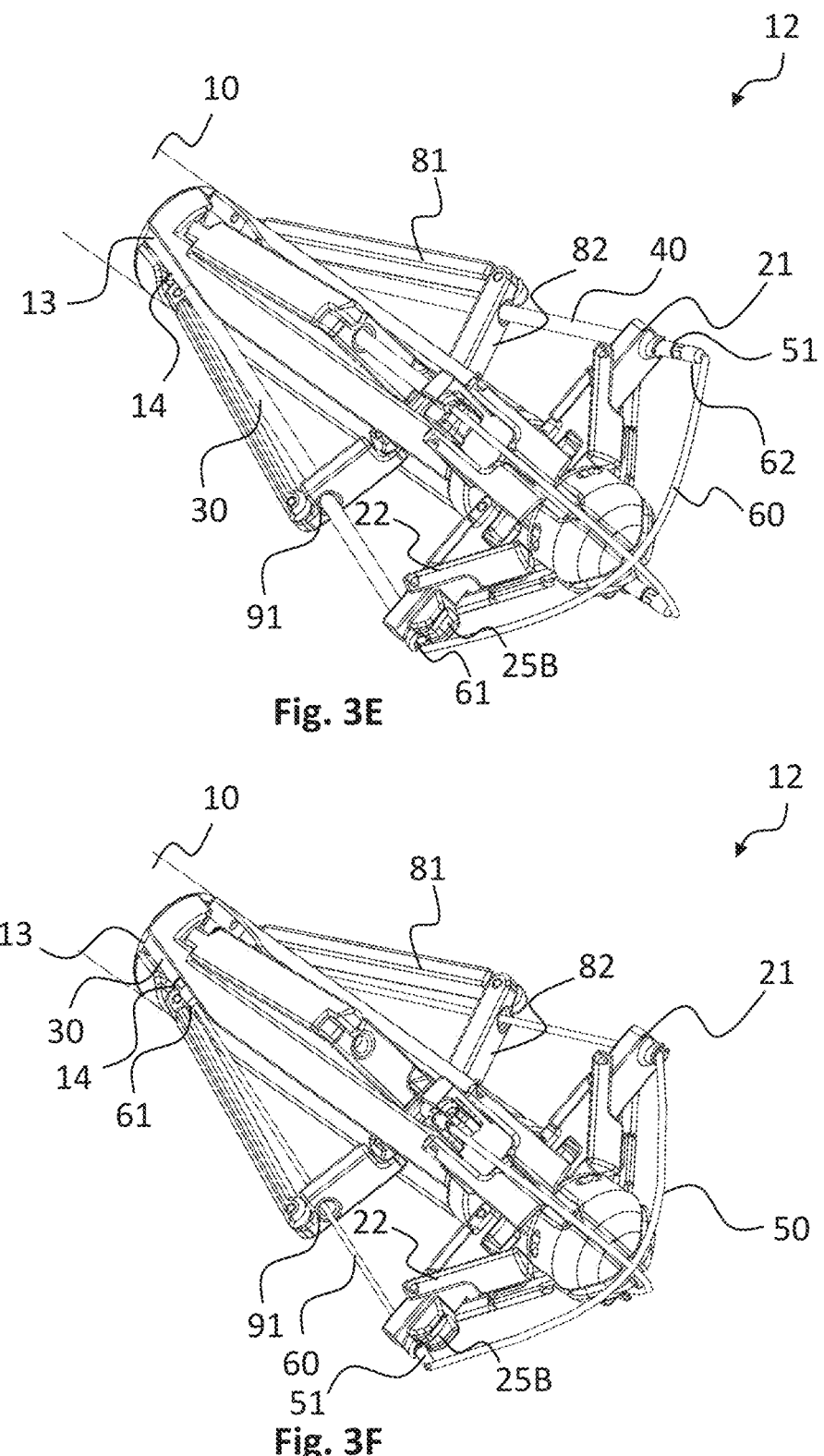

In FIG. 3E, the second needle 40 is coupled to the second connector 62 via the releasable tip 51. The needle 40 is used to exert a distal pushing force on the second connector 62. When the pushing force reaches a predetermined threshold, the retainer 23 on the support arm 21 releases the second connector 62 from the support arm 21.

Subsequently, as shown in FIG. 3F, the hollow second needle 40 is retracted back into the exit opening 14 of the elongate shaft 10, while the second suture 50 remains connected to the second connector 62 via the tip 51.

The first needle 30 connected to the first connector 61 is pulled proximally beyond a predetermined threshold and retrieved back into the exit opening 14 of the elongate shaft 10, thereby also pulling the connected sutures 50, 60 in the proximal direction of the elongate shaft 10. The protrusion on the distally facing side of the support arm 21 with the groove 25B may be used to guide the sutures 50, 60 during the pulling motion.

Figures 3G, 3H:
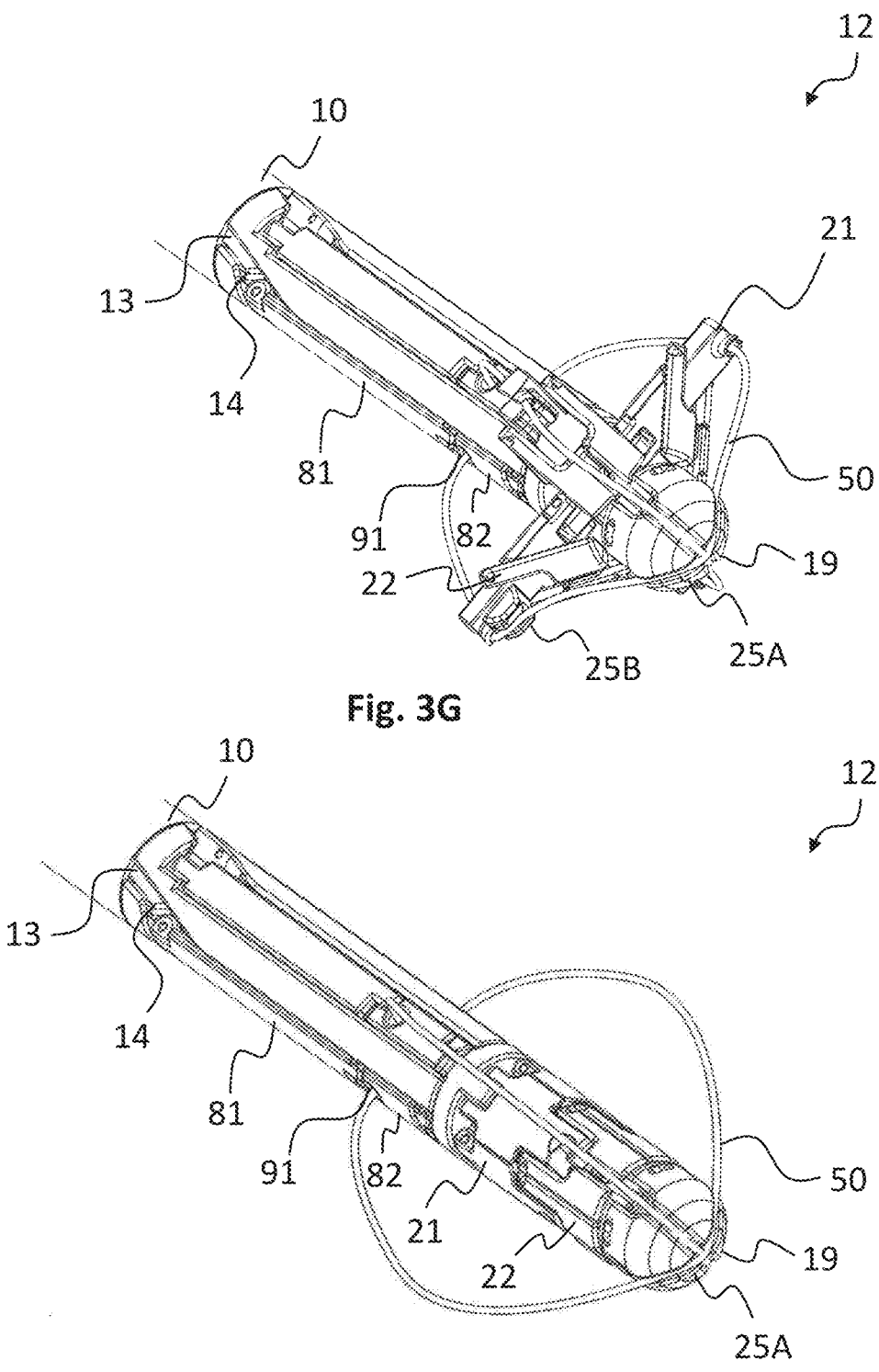

Subsequently, in FIGS. 3G and 3H, the expandable pushing member 80, the expandable guide member 90 and the support structure 20 of the device 1 are moved back to its contracted configuration, whereas the sutures 50, 60 are released from the device 1 by pulling the device 1 in the proximal direction. The two released sutures 50 (of the first and second pairs of needles) may thus form two half loops around the tissue opening 101 which form a cross-stitch. The sutures 50 are then tied to a knot by the user, thereby closing the tissue opening 101.

FIGS. 4A-4D provide additional cross-sectional schematic illustrations of the device 1.

Figure 4A:
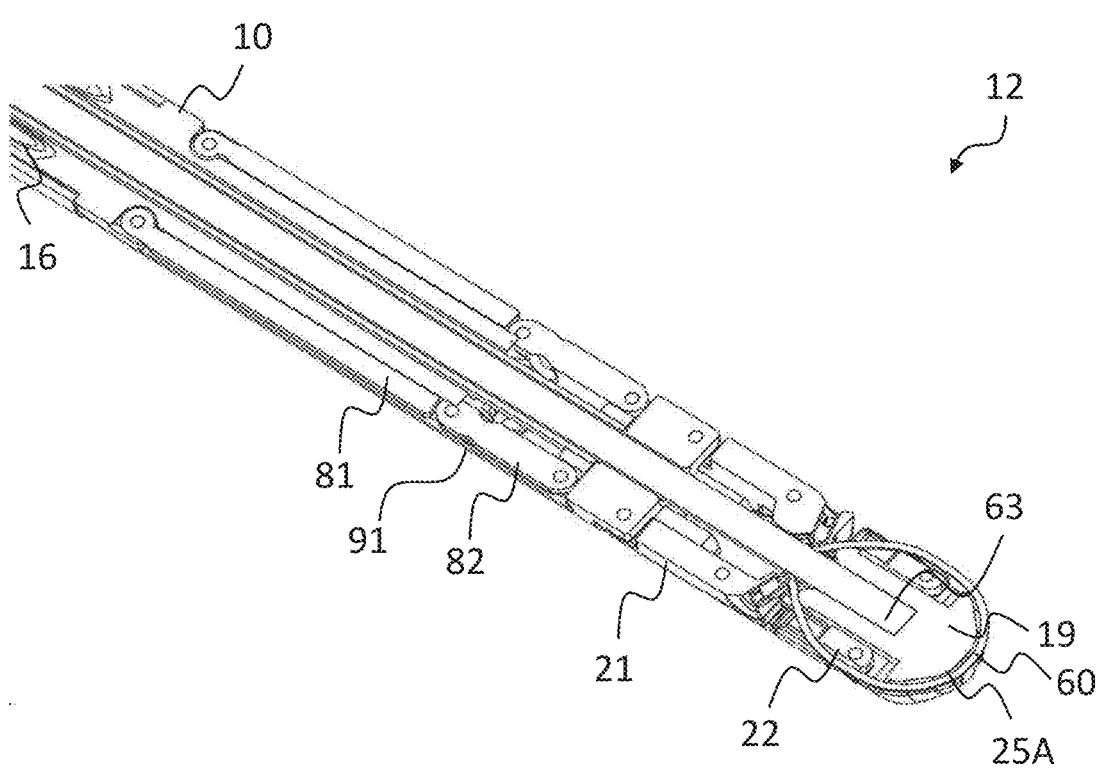
FIG. 4A-4D are schematic cross-sectional perspective views showing the device of FIG. 1 at its distal end during individual operation steps performed for the closure of a tissue opening.
Figure 4B:
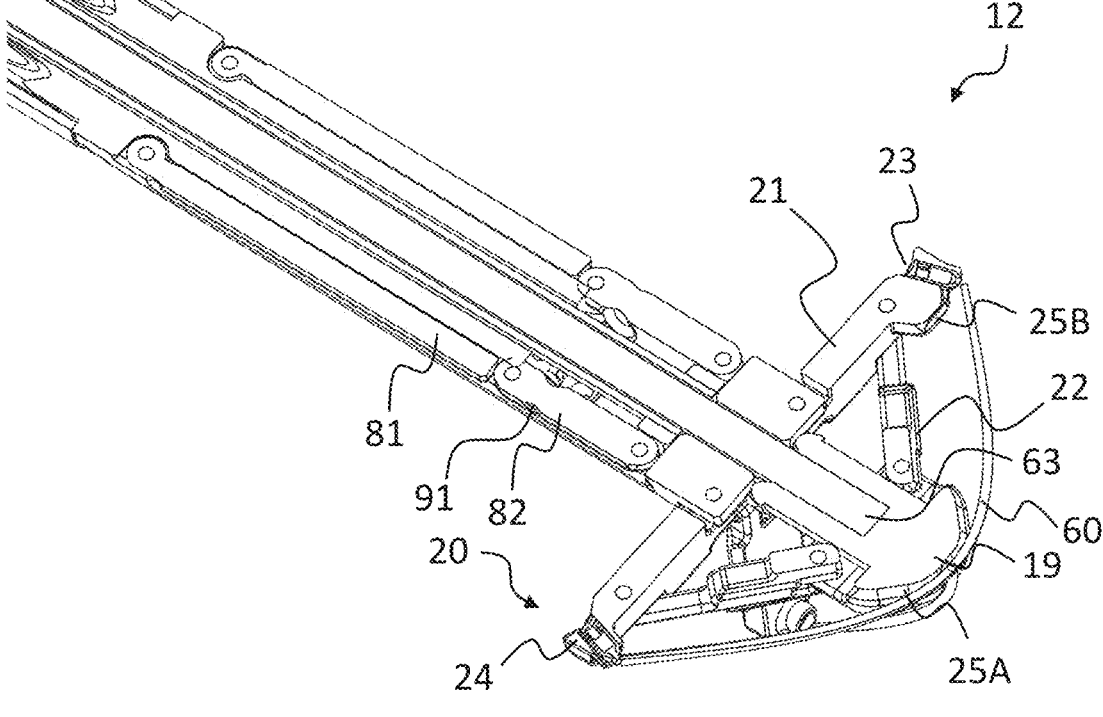

As shown in these figures, the first actuation member 63 may be formed as a rod connected to the distal tip 19. The rod is movable between a first position and a second position along the longitudinal axis $A_L$ to shift the support structure 20 between its contracted and expanded configurations as shown in FIGS. 4A and 4B, respectively. The first actuation member 63 is pulled in the proximal direction for expanding the support structure.

Figure 4C:
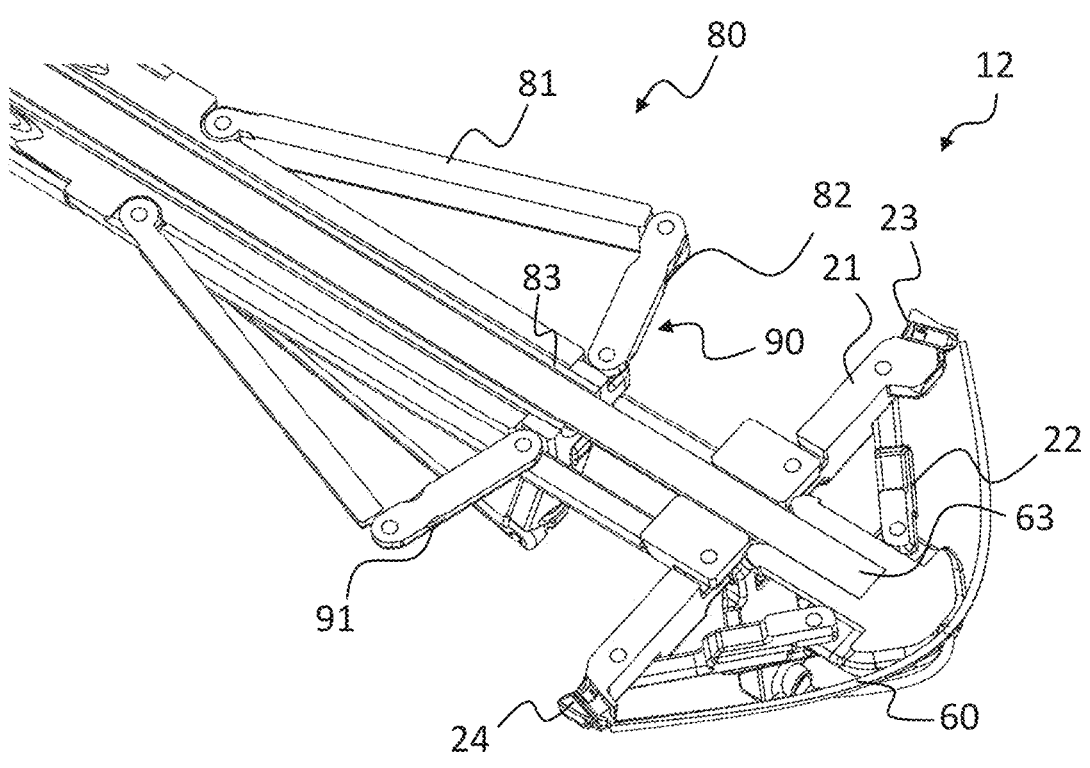

FIG. 4C illustrates the expandable pushing member 80 and the expandable guide member 90 being deployed from their contracted configuration to the expanded configuration by the second actuation member 83, which is formed as a sleeve, moving between a first position and a second position along the longitudinal axis $A_L$. The second actuation member is pulled in the proximal direction for moving the pushing member 80 and the guide member 90 to the expanded configuration.

Figure 4D:
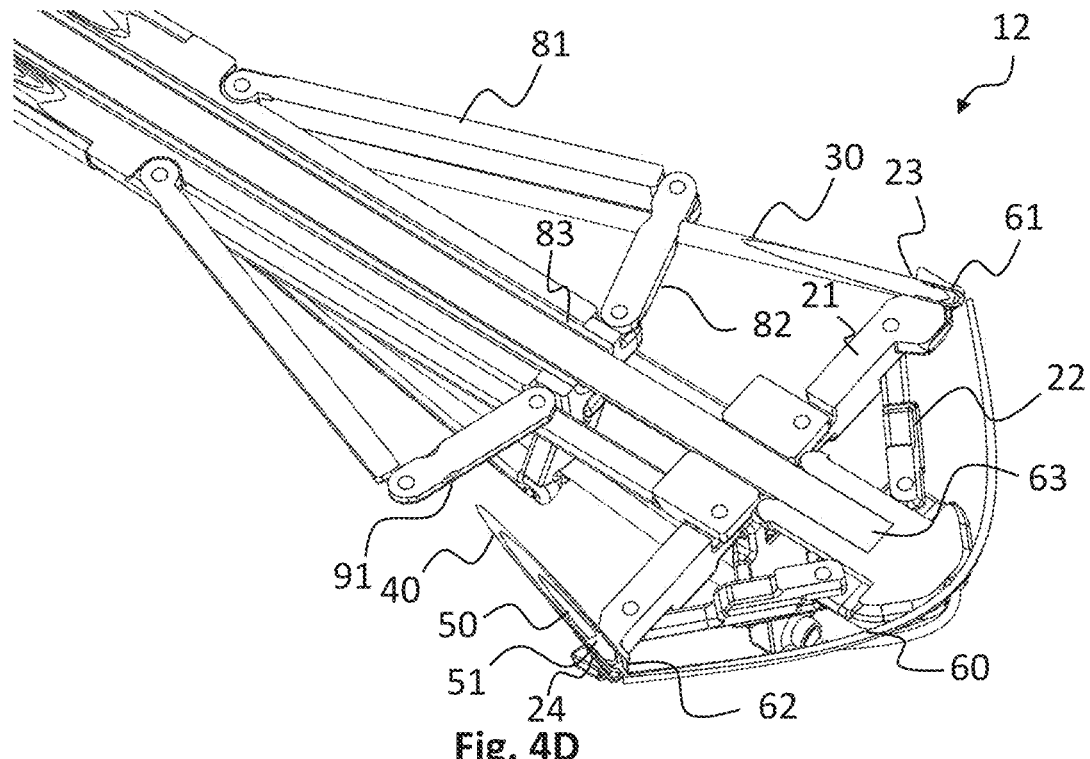

FIG. 4D further shows the cross section of the first needle 30, which may be a solid needle devoid of a needle lumen, and the second hollow needle 40 comprising the releasable tip 51 attached to the second suture 50. The orientation of the guide openings 91 in the expandable guide member 90 matches the oblique trajectories of the needles 30, 40.

The second hollow needle 40 comprising a needle lumen extending therethrough can be configured to inject fluid through said lumen, such as growth factors or glue, into the tissue 100.

If desired, also the first needle could be a hollow needle with a lumen and could be used to inject fluid therethrough.

Figure 5:
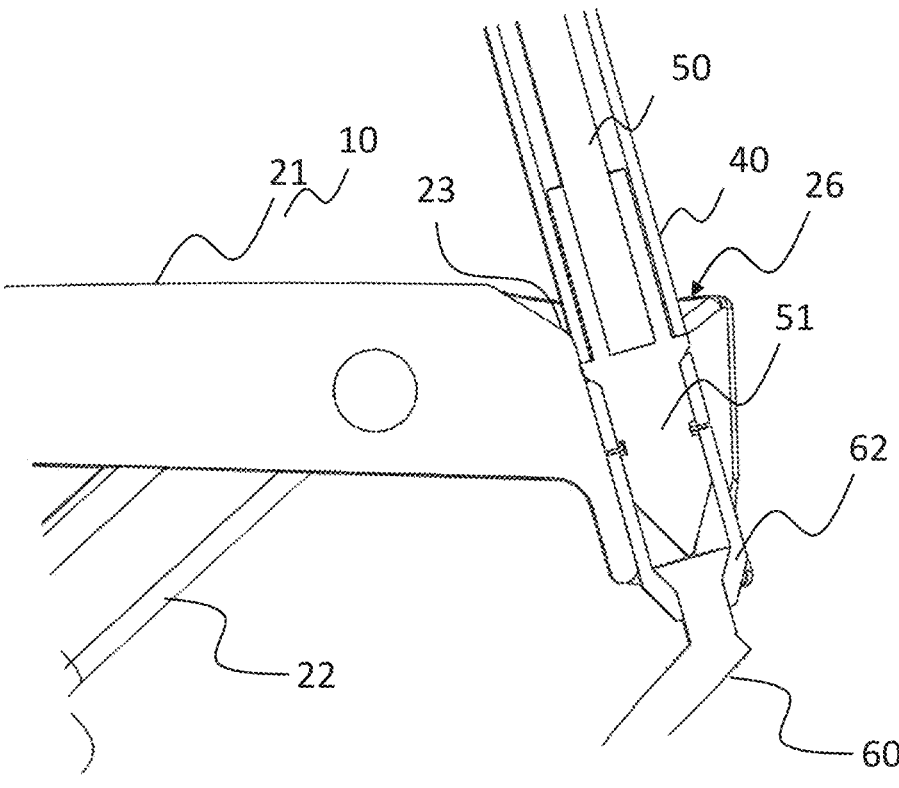
FIG. 5 is a schematic cross-sectional detail of a support structure of the device of FIG. 1, wherein the second needle is shown coupled to a respective coupler.

The cross-sectional detail shown in FIG. 5 schematically illustrates the connection of the releasable tip 51 of the second needle 40 to the second connector 62 retained in the retainer 23 of the support arm 21. The retainer 23 is surrounded by a funnel-shaped guiding surface 26. This may be helpful for guiding the respective needle if a minor deviation from the intended trajectories occurs. The second suture 50 attached to the releasable tip 51 is coupled and retained by the second connector 62 by a form fit or a press fit coupling. As shown, the first suture 60 is fixedly connected to the second connector 62 and likewise to the first connector 61.

Figure 6:
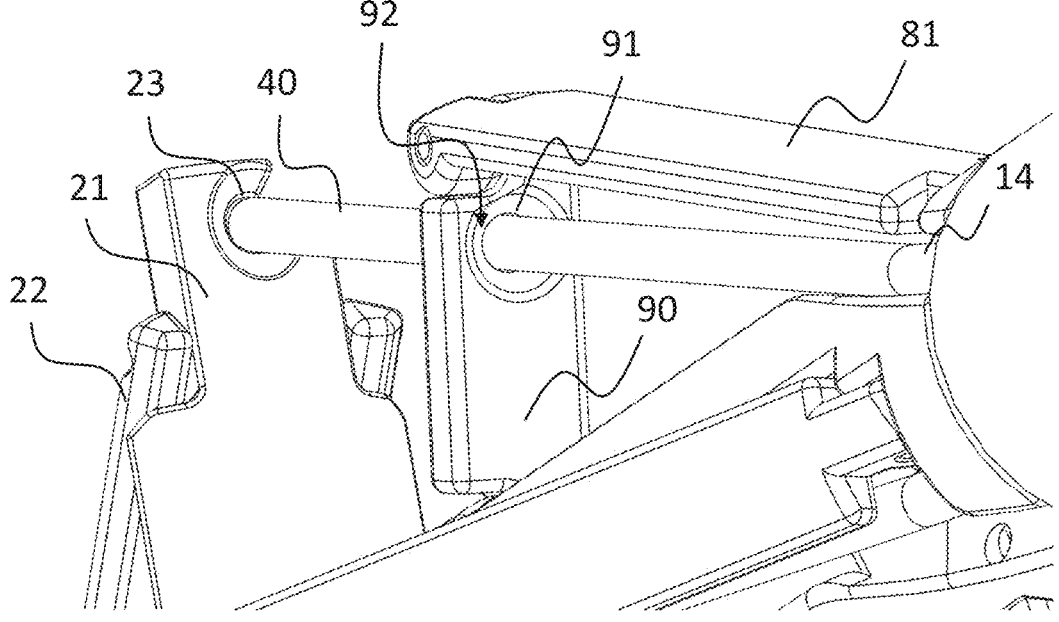
FIG. 6 is a schematic perspective view of the support structure of the device of FIG. 1 connected with the second needle showing an expandable pushing member and an expandable guide member.

The perspective detail shown in FIG. 6 illustrates the trajectory of the second needle 40 extending through the expandable guide member 90 to the support structure 20. The guide opening 91 may be surrounded by a funnel-shaped guiding surface 92 at its proximally facing side.

Figure 7A:
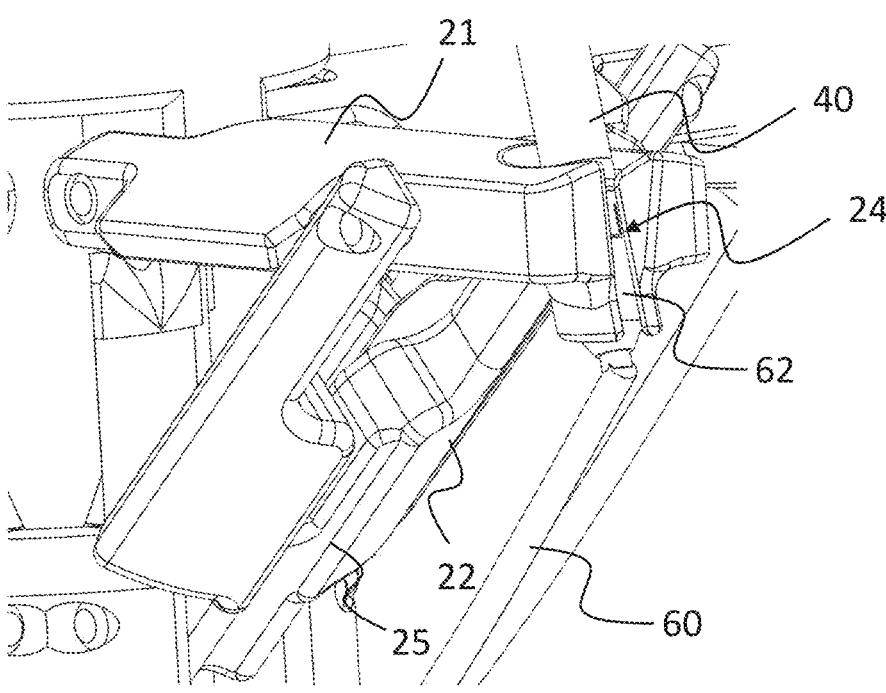
FIG. 7A-7B are schematic perspective views of the second connector being connected with the second needle and being pushed through a respective retainer.
Figure 7B:
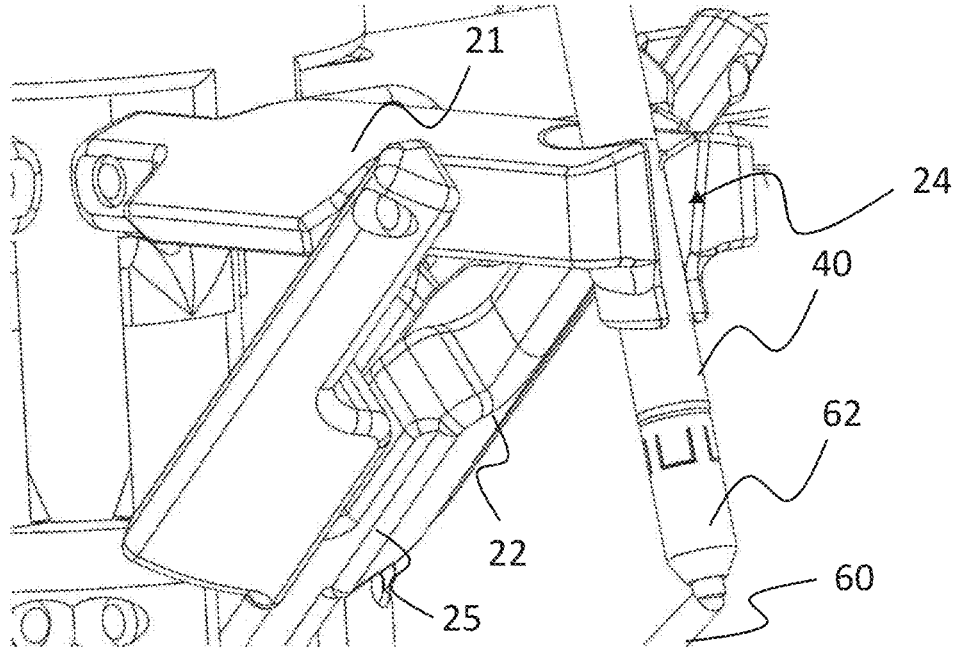

FIGS. 7A and 7B illustrate the motion of the second needle 40 while pushing the retainer 23 distally and exceeding a predetermined threshold distal pushing force. One or both of the retainers 23 may be provided with a release opening 24 or slot for subsequently releasing the suture 50, 60, 70 from the support arm 20 when the device is pulled out of the patient's body. The groove 25 at the support links 22 allows for the accommodation of the first suture 60 at the beginning of the procedure when the support structure 20 is in the contracted configuration.

Figure 8A:
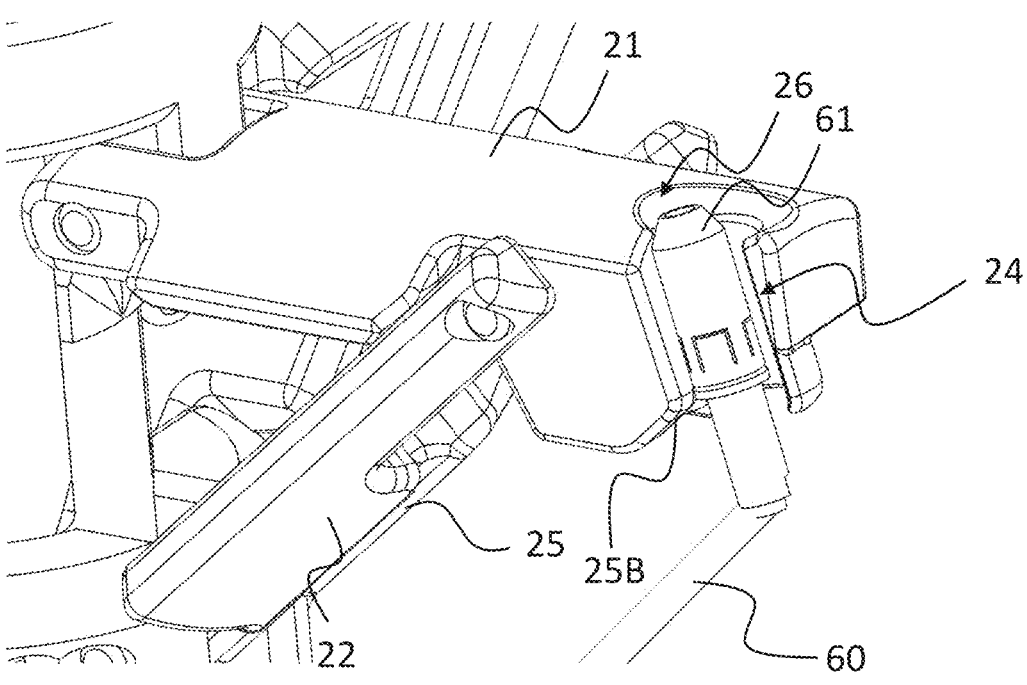
FIG. 8A-8B are schematic perspective views of a first connector of the support arm being connected with the first needle to be retrieved by the first needle.
Figure 8B:
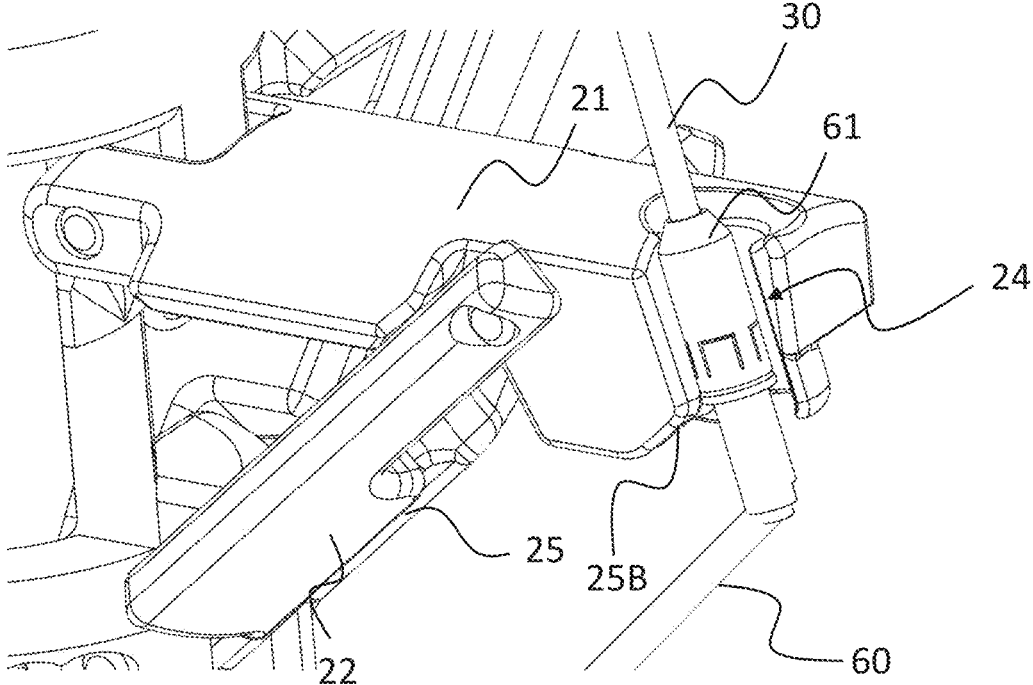

FIGS. 8A and 8B illustrate the motion of the first needle 30 coupling to the first connector 61 retained in the retainer 23 of the opposing support arm 21, which can later be retrieved or pulled in the proximal direction into the exit opening 14 of the elongate shaft 10. The first needle 30 can be coupled with the first connector 61 via a form fit or a press fit coupling. The support arm 21 related to the first connector 61 may comprise a groove or a channel 25 on its distal surface to guide the sutures 50, 60 when being pulled in the proximal direction. The protrusion on a distal facing side of the support arm 21 with a groove 25B or a channel can be used to guide the sutures 50, 60 when they are pulled in the proximal direction. Furthermore, a release opening 24 and a funnel-shaped guiding surface 26 may be located on the support arm 21.

As described above, the flaps 81 and/or the links 91 may be made from or comprise a material that has a high ultrasound visibility and/or is radiopaque. This allows a user to see whether the second tissue layer 103 has been adequately moved (see FIG. 2B). For example, an ultrasound and/or radiopaque marker may be provided on the flaps 81 and/or on the links 91. Alternatively, the flaps 81 and/or links 91 may be made from or coated with an ultrasound visible material and/or a radiopaque material, as described above.

The support structure 20, optionally at least the support arms 21, may be made from an ultrasound visible material and/or a radiopaque material as well, or comprise such marker. This may help the user to determine if the support structure has been adequately expanded distally of the tissue opening 101.

FIGS. 9-14 each illustrate a device 1 according to further embodiments of the present disclosure.

Figure 9:
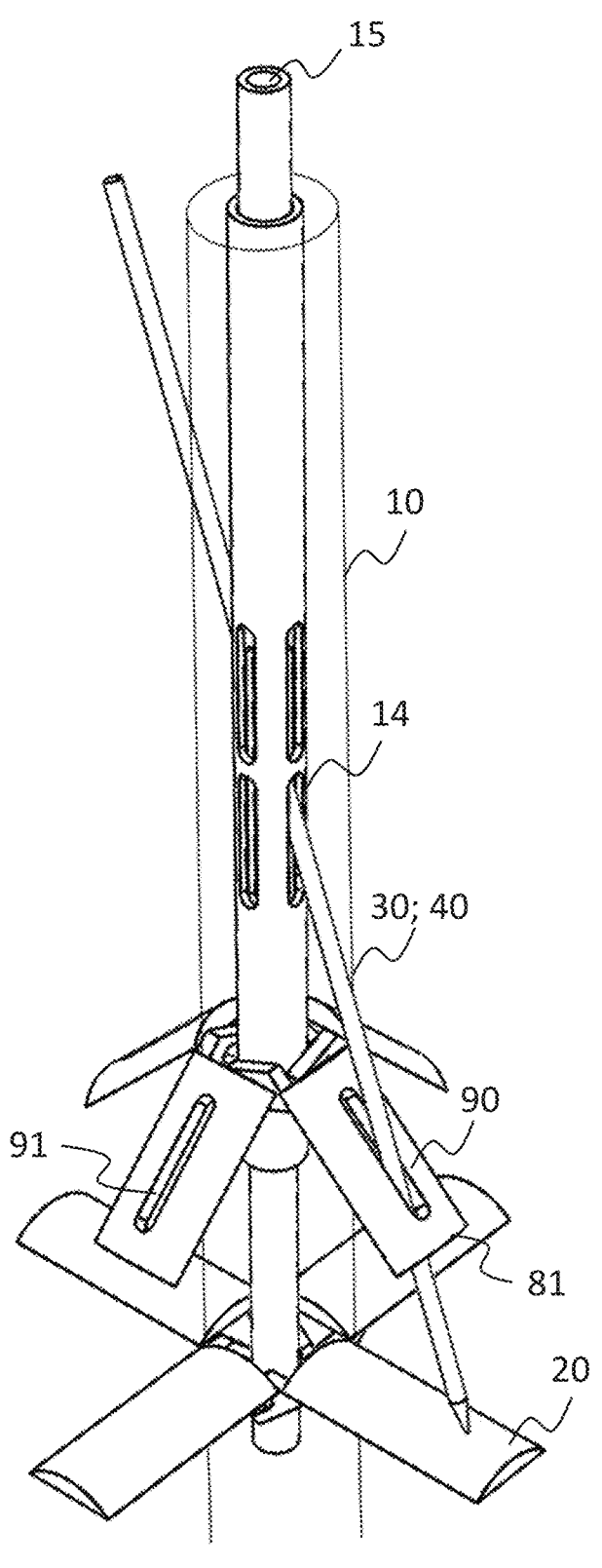
FIG. 9 is a schematic perspective view of a device according to a further embodiment of the present invention, in which the expandable guide member is located on the flaps of the expandable pushing member.

FIG. 9 schematically illustrates a device 1 according to a further embodiment in which the expandable guide member 90 and its guide openings 91 are located on the flaps 81 of the expandable pushing member 80. As a result, the exit openings 14 are designed to be positioned above the expandable pushing member 80, and the trajectories of the needles 30, 40 are adjusted accordingly. FIG. 9 also illustrates a lumen 15 extending along the longitudinal axis $A_L$ of the elongate shaft 10 and of the distal tip 19, in which a long first suture 60 can be stored. The elongate shaft 10 and the first actuation member 63 comprises at least one distal opening through which the first suture 60 may enter into the lumen 15. At least one loop of the first suture 60 can be formed outside of a proximal end of the lumen 15 or in the lumen 15.

FIGS. 10A-10D schematically illustrate the device 1 according to a further embodiment in cross-sectional perspective views. FIGS. 10A-10D show details of the distal end 12 of the device 1, as indicated by the circled area in FIG. 1. The deployment mechanism of the support structure 20, the expandable pushing members 80 and the expandable guide members 90 correspond to those described above. Therefore, only the differences will be highlighted in the following.

Figure 10A:
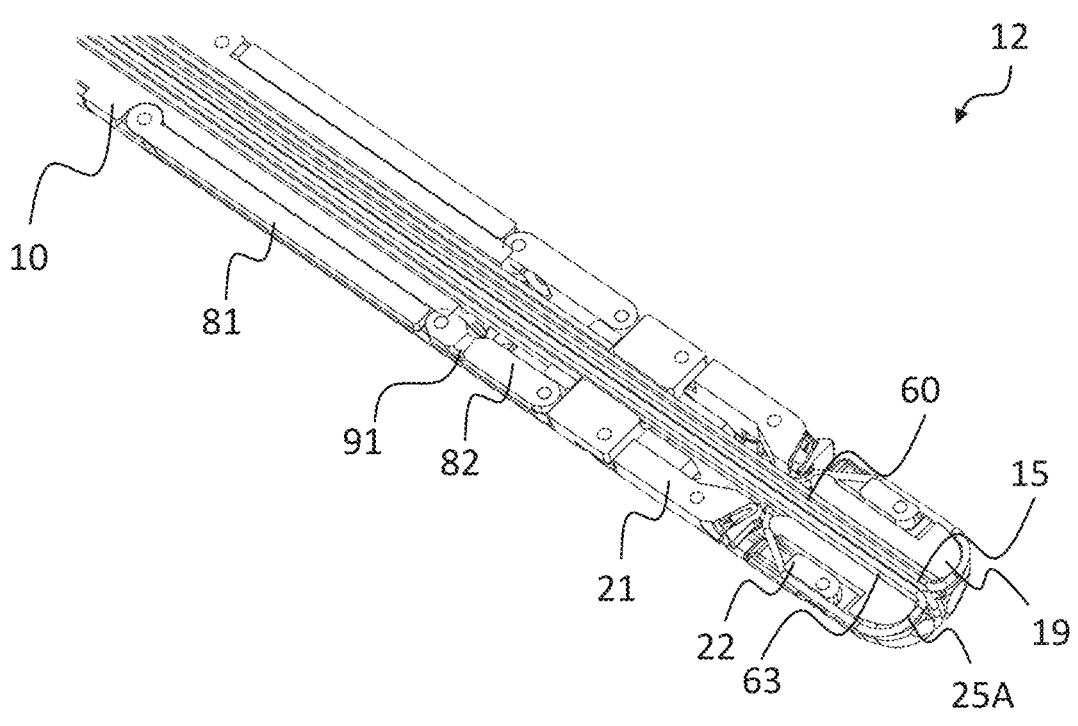
FIGS. 10A-10D are schematic cross-sectional perspective views showing a device according to a further embodiment of the present invention at its distal end during individual operation steps performed for the closure of a tissue opening.
Figure 10B:
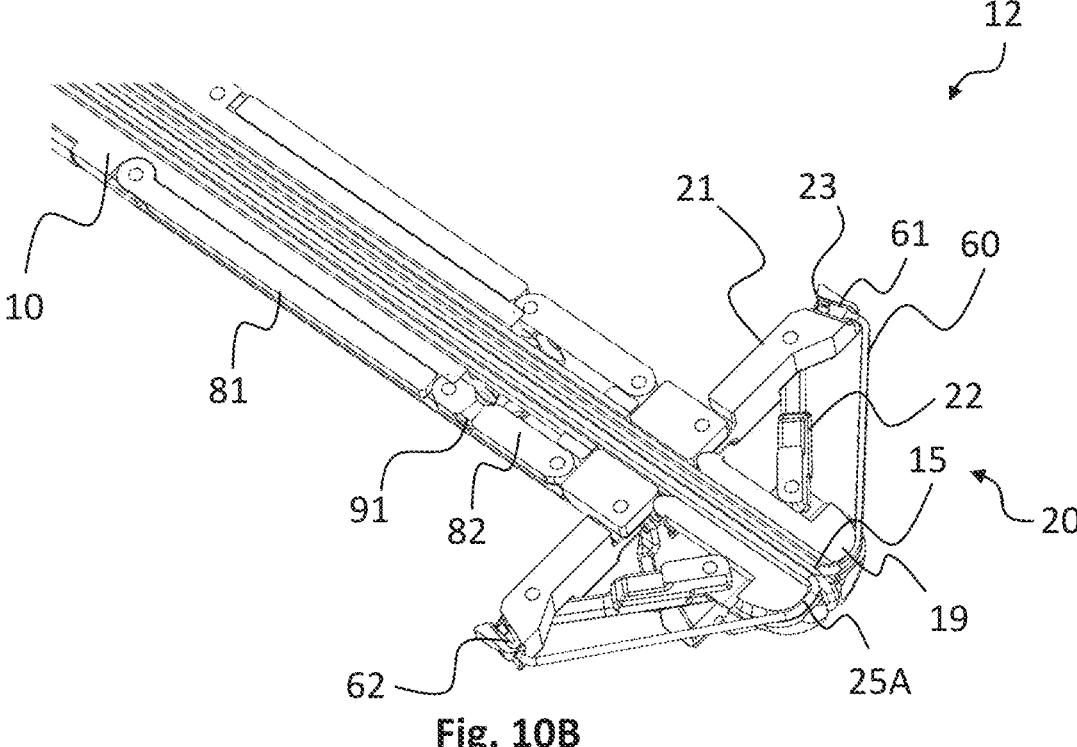

Referring to FIGS. 10A and 10B, the elongate shaft 10 comprises a lumen 15 extending along the longitudinal axis $A_L$ that stores a first suture 60. This suture may be considerably longer than the first suture 60 of the embodiment discussed with reference to FIGS. 1 to 8.

As shown in FIGS. 10A and 10B, the suture 60 extends from the distal tip 19 along the lumen 15 in a proximal direction. Optionally, at least two sutures 60 extending through the lumen in this manner, i.e, the one suture for each pair of needles. Each of the sutures 60 optionally forms a loop, either inside the lumen 15 or at a proximal end of the device. Each suture 60 extends between, and is fixedly coupled to, first and second connectors 61, 62 for a respective pair of needles 30, 40. Such suture 60 eliminates the need of connecting another suture 50; 70 to the first suture 60. In other words, the suture 60 does not act as a transfer suture, but may be a suture which is subsequently tied to close the tissue opening 101.

Figure 10C:
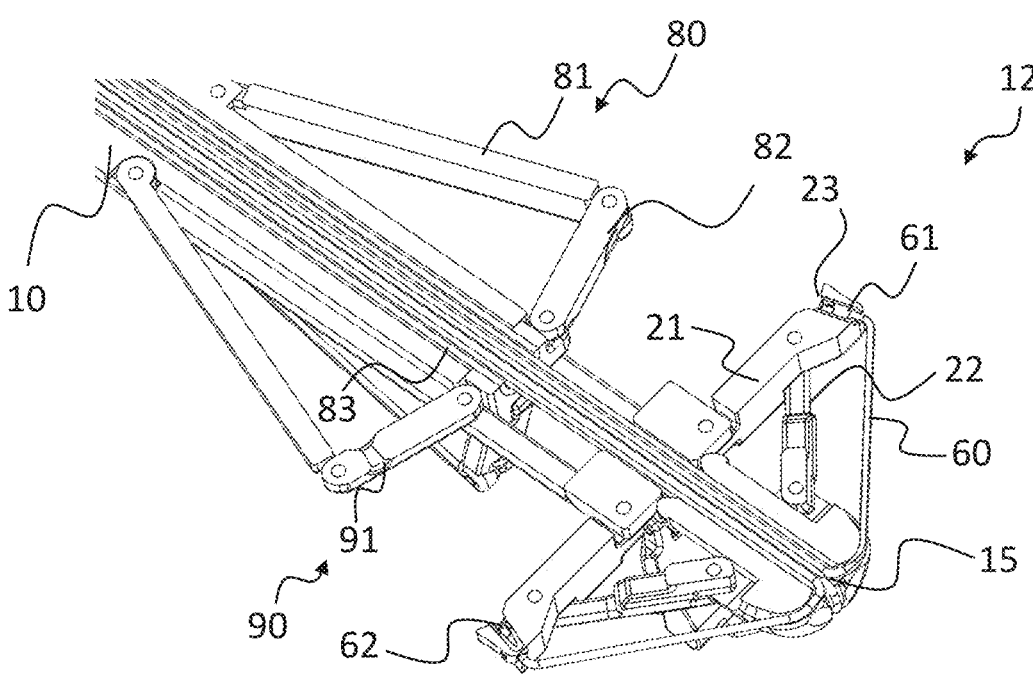
Figure 10D:
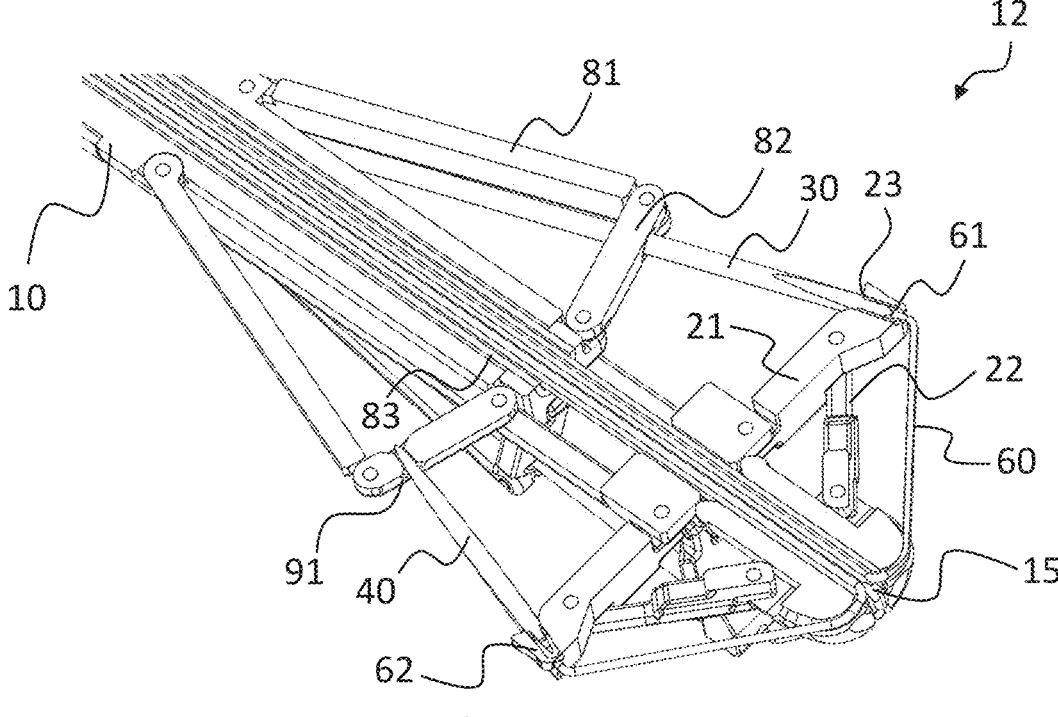

Furthermore, as shown in FIGS. 10C and 10D, the at least one first and second needles 30, 40 may be solid needles devoid of a needle lumen. The needles connect to the connectors 61, 62, respectively and retrieve the respective connector 61, 62 by pulling it proximally into (and through) the respective needle guide in the elongate shaft 10. In this manner a half-loop for each suture 60 is formed around the tissue opening 101, which, after being released from the device 1, can be tied into a knot. The two sutures may form a cross stitch.

Figure 11A:
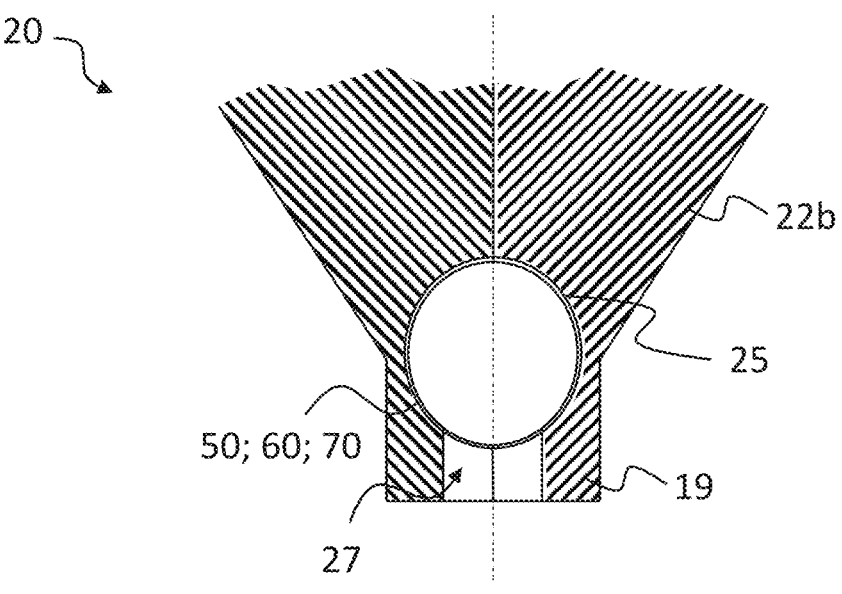
FIGS. 11A-11B are schematic cross-sectional front views of a mechanism for releasing a suture, thread or wire from at least one channel or groove of the devices according to the present invention.
Figure 11B:
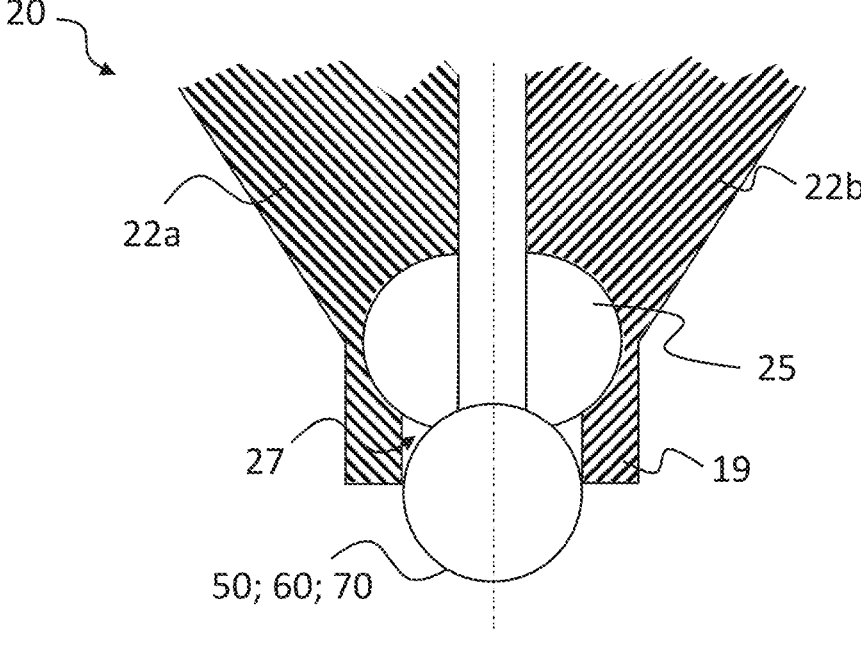

FIGS. 11A and 11B schematically illustrate a device 1 according to a further embodiment. In this embodiment, at least one channel or groove 25 is provided in the support structure 20 and/or at the distal tip 19. The channel or groove 25 is configured to retain the at least one suture 50, 60, 70 in a first, closed configuration and to release the at least one suture 50, 60, 70 retained therein in a second, open configuration.

For this purpose, a slot 27 may be provided, which in the first, closed configuration has a width or diameter smaller than the suture 50, 60, 70 and in the second, open configuration has width or diameter larger than the suture 50, 60, 70. Such release mechanism can be implemented in different ways. As shown in FIG. 111B, the support structure 20 can be designed as a two-part structure with two parts that move away from each other in order to form or widen the slot 27. For example, each of the support links 22 described above may be formed by two separate parts 22a, 22b that are movable with respect to each other. The channel or groove 25 is formed by these two parts 22a, 22b. The parts 22a, 22b move away from each other to form or widen the slot 27.

Figure 12A:
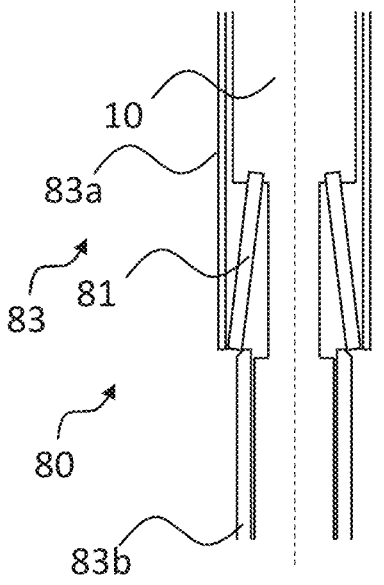
FIGS. 12A-12B are schematic cross-sectional front views of another actuation mechanism for the expandable pushing member that may be employed in the devices according to the present invention.
Figure 12B:
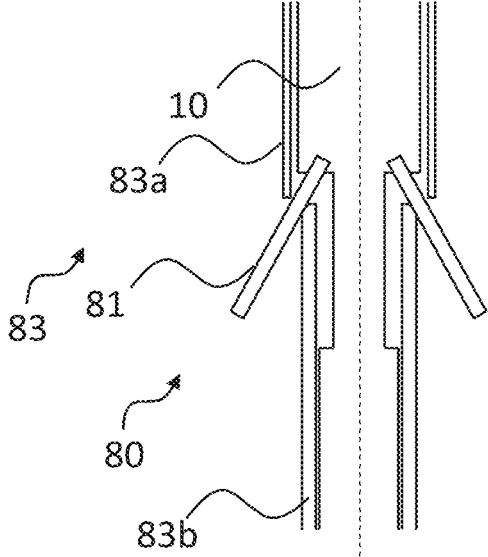

FIGS. 12A and 12B schematically illustrate the device 1 according to a further embodiment with the second actuation member 83 in form of a sleeve used to move the flaps 81 of the expandable pushing member 80. As illustrated in FIG. 12A, a first portion 83a of the second actuation member 83 is configured to maintain the expandable pushing member 80 in the contracted configuration by at least partially covering the flaps 81 when in a first position. In a second position (FIG. 12B), the second actuation member 83 allows the flaps 81 to move radially outward to the expanded configuration. In the second position, the outer sleeve 83 is pulled in the proximal direction to expose the flaps 81.

The flaps 81 may be biased radially outward, e.g. by being made from an elastic material and/or being connected to the elongate shaft 10 by a spring hinge.

Alternatively or additionally, a second portion 83b of the second actuation member 83 may be used to move the flaps 81 radially outward. The second portion 83b may slide be pulled in the proximal direction to slide between the shaft and the flaps 81 (FIG. 12B) and thereby open the flaps 81 radially outward from the contracted configuration to the expanded configuration. By pushing the outer sleeve 83 and the inner slider in the distal direction, the flaps 81 can be closed. When using such sleeve with a second portion 83b, the flaps 81 can be closed by the first portion 83a as described above. Alternatively, the flaps could be biased in the radially inward direction. e.g. by being made from an elastic material and/or being connected to the elongate shaft 10 by a spring hinge. It will thus be appreciated that the first and second sections 83a, 83b may be provided in conjunction or independently from each other.

Figure 12C:
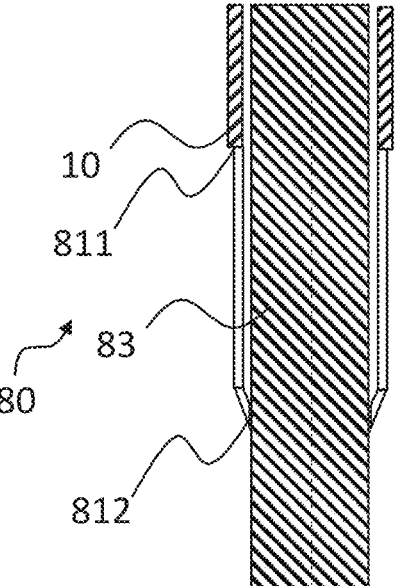
FIGS. 12C-12D are schematic cross-sectional front views of a further expandable pushing member that may be employed in the devices according to the present invention.
Figure 12D:
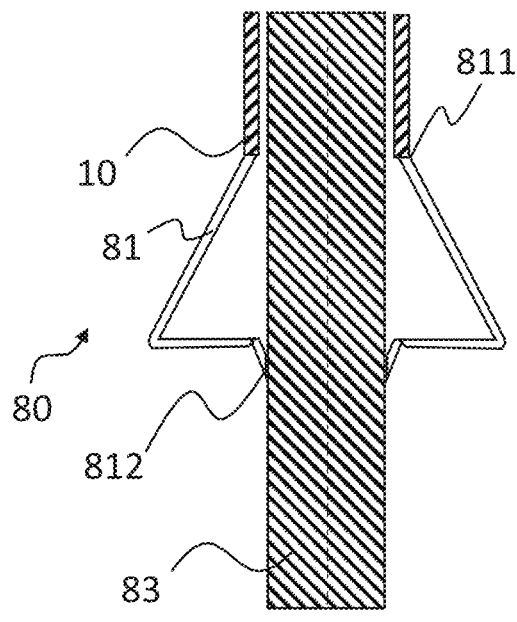

FIG. 12C-12D schematically illustrate the device 1 according to a further embodiment. As shown, the flaps 81 of the expandable pushing member 80 can be formed as one or more sheets that bulge(s) outwards. Such outwardly bulging movement can be achieved by moving a first portion

811 of the sheet towards a second portion 812 of the sheet. Depending on how the sheet is connected, the movement can be achieved by moving the first or second actuation member with respect to the elongate shaft, or by moving the first actuation member with respect to the second actuation member.

The sheet is optionally thin.

The sheet is optionally made of metal, polymer or nitinol.

Each flap 81 can be formed as a separate sheet or one or more (e.g., all) of the flaps 81 can be formed in a tubular body (e.g., by cutting out the material between the flaps 81, as for example by laser cutting a thin tubular body).

As described above for the embodiment of FIGS. 1 to 8B, a portion 811 (e.g., a first end) of the flaps 81 may be connected, for example, to the elongate shaft 10. A second portion 812 (e.g., a second end) of the sheet may be connected to, e.g., the second actuation member 83. The movement of the second actuation member 83 in the proximal direction may then force the sheet to bend or bulge outwards (see FIG. 12D).

The bulging shape of the sheet is optionally achieved by the one or more living hinges formed at the positions of the first, second and/or third hinges as described above. Alternatively, an embodiment without such living hinges is also considered. While the sheet may assume a more "rounded" shape in this case, this may be sufficient for certain applications.

The sheet may further comprise at least one opening through which the needles 30, 40 may pass. Such opening may function as a guiding member, as described above.

Figure 13:
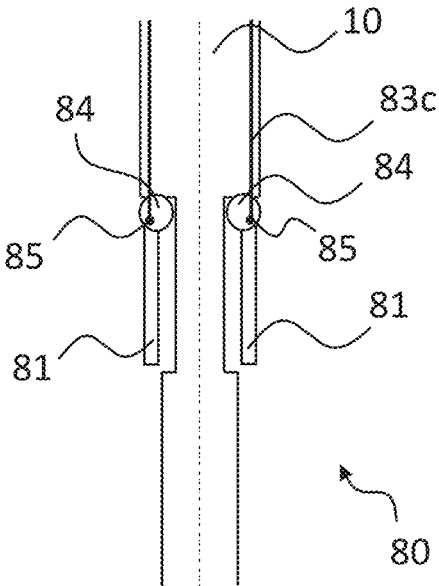
FIG. 13 is a schematic cross-sectional front view of a further actuation mechanism for the expandable pushing member that may be employed in the devices according to the present invention.

As shown in FIG. 13, which schematically illustrate the device 1 according to a further embodiment, it is possible to operate the flaps 81 by the use of a second actuation member in the form of one or more wires 83c coupled to the flaps 81. Each flap 81 rotates around a hinge 84 when moving the expandable pushing member 80 from the contracted configuration to the expanded configuration. The wire(s) 83c may be coupled to the flaps at the hinge at a position 85 that is eccentrical to the axis around which the respective flap 81 rotates.

Figure 14:
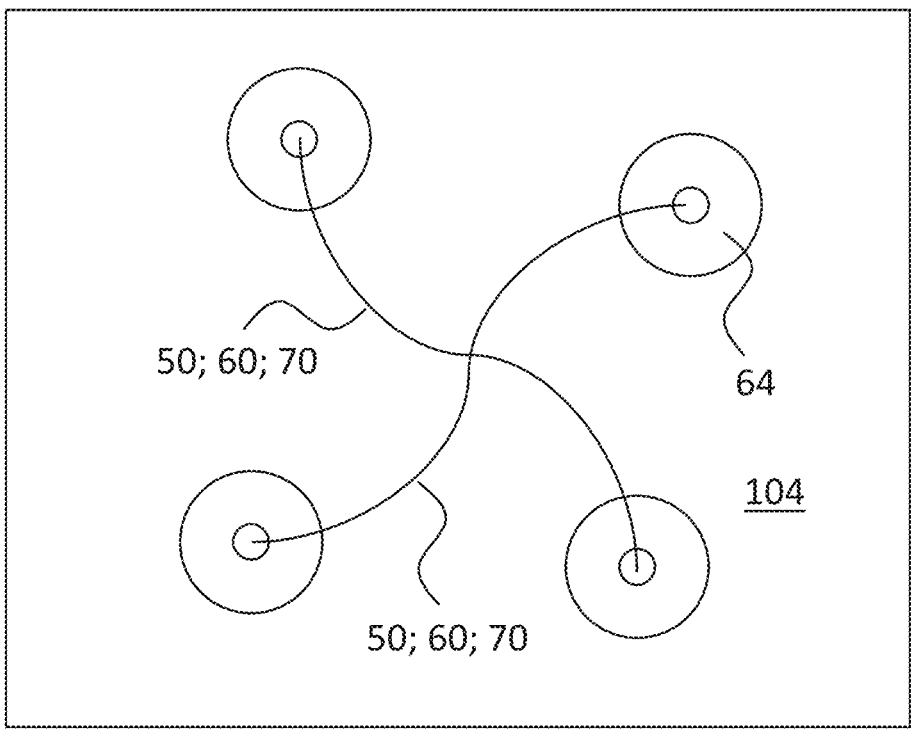
FIG. 14 is schematic perspective view of a second tissue layer of the tissue with sutures and washers according to the present invention, as seen from within a body cavity.

FIG. 14 schematically illustrates two sutures 50, 60, 70 with washers 64 covering the stitching holes in the second tissue layer 104 penetrated by the first and second needles 30, 40. The washers 64 are arranged on the suture 50, 60, 70 in such manner that they are located within the body cavity 105 after the tissue opening 101 is closed in abutment against the second tissue layer 104. Alternatively or additionally, at least one patch (not illustrated) that is configured to remain in the body cavity 105 and overlap with the closed tissue opening 101 from within the cavity 105 may be used.

The invention may be defined, for example, by the following aspects:

1. A device (1) for closing a tissue opening (101) in a tissue (100) with at least one suture (50, 60, 70), the tissue extending at least partially around a body cavity (105) and comprising at least first and second tissue layers (103, 104), the second tissue layer (104) extending between the first tissue layer (103) and the body cavity (105), the device (1) comprising:

an elongate shaft (10) having a proximal end (11), a distal end (12) and extending along a longitudinal axis ($A_L$), the elongate shaft (10) configured to be inserted into the tissue opening (101) in the tissue (100), the elongate shaft (10) comprising a plurality of needle guides (13), each needle guide (13) having an exit opening (14) at its distal end;

a support structure (20) at the distal end (12) of the
elongate shaft (10) configured to move between a
first, contracted configuration and a second,
expanded configuration the support structure (20)
being configured to be expanded in the body cavity
(105);
at least one first needle (30) and at least one second
needle (40);
at least one first connector (61) and at least one second
connector (62) coupled to the support structure (20),
the first connector (61) being configured to couple
with the first needle (30), optionally with a distal end
of thereof, and the second connector (62) being
configured to couple with the second needle (40),
optionally with a distal end thereof;
wherein each of the needles (30, 40) is configured to be
translated along a respective one of the needle guides
(13), the first needle (30) being configured to be
advanced out of the exit opening (14) of the respec-
tive needle guide (13) and to penetrate through the
second tissue layer (104) along a first trajectory, the
first trajectory extending from the exit opening (14)
through the second tissue layer (104) obliquely to the
longitudinal axis (A$_L$) to the first connector (61), and
the second needle (40) being configured to be
advanced out of the exit opening (14) of the respec-
tive needle guide (13) and to penetrate through the
second tissue layer (104) along a second trajectory,
the second trajectory extending from the exit open-
ing (14) through the second tissue layer (104)
obliquely to the longitudinal axis (A$_L$) to the second
connector (62); and
at least one expandable pushing member (80) config-
ured to push the first tissue layer (103) out of the first
and second trajectories, the pushing member (80)
being configured to move between a contracted
configuration and an expanded configuration.
2. A device (1) for closing a tissue opening (101) in a
tissue (100) with at least one suture (50, 60, 70), the
tissue extending at least partially around a body cavity
(105) and comprising at least first and second tissue
layers (103, 104), the second tissue layer (104) extend-
ing between the first tissue layer (103) and the body
cavity (105), the device (1) comprising:
an elongate shaft (10) having a proximal end (11), a
distal end (12) and extending along a longitudinal
axis (A$_L$), the elongate shaft (10) configured to be
inserted into the opening (101) in the tissue (100),
the elongate shaft (10) comprising a plurality of
needle guides (13), each needle guide (13) having an
exit opening (14) at its distal end;
a support structure (20) at the distal end (12) of the
elongate shaft (10) configured to move between a
first, contracted configuration and a second,
expanded configuration the support structure (20)
being configured to be expanded in the body cavity
(105);
at least one first needle (30) and at least one second
needle (40);
at least one first connector (61) and at least one second
connector (62) coupled to the support structure (20),
the first connector (61) being configured to couple
with a distal end of the first needle (30) and the
second connector (62) being configured to couple
with a distal end of the second needle (40);
wherein each of the needles (30, 40) is configured to be
translated along a respective one of the needle guides

26

(13), the first needle (30) is configured to be
advanced out of the exit opening (14) of the respec-
tive needle guide (13) and to penetrate through the
second tissue layer (104) along a first trajectory, the
first trajectory extending from the exit opening (14)
through the second tissue layer (104) obliquely to the
longitudinal axis (A$_L$) to the first connector (61), and
the second needle (40) is configured to be advanced
out of the exit opening (14) of the respective needle
guide (13) and to penetrate through the second tissue
layer (104) along a second trajectory, the second
trajectory extending from the exit opening (14)
through the second tissue layer (104) obliquely to the
longitudinal axis (A$_L$) to the second connector (62);
and
at least one expandable guide member (90) configured
to guide the at least one first and the at least one
second needles (30, 40) along their respective tra-
jectory, the guide member (90) being configured to
move between a contracted configuration and an
expanded configuration, wherein the guide member
(90) overlaps with the first and second trajectories in
the expanded configuration.
3. The device (1) according to aspect 1, wherein the
device (1) comprises at least one expandable guide
member (90) configured to guide the at least one first
and the at least one second needles (30, 40) along their
respective trajectory, the guide member (90) being
configured to move between a contracted configuration
and an expanded configuration, wherein the guide
member (90) overlaps with the first and second trajec-
tories in the expanded configuration.
4. The device (1) according to aspect 2, wherein the
device (1) comprises at least one expandable pushing
member (80) configured to push the first tissue layer
(103) out of the first and second trajectories, the push-
ing member (80) being configured to move between a
contracted configuration and an expanded configura-
tion.
5. The device (1) according to any one of the preceding
aspects, wherein the first and second trajectories are
partially in a cavity created between the pushing mem-
ber (80) and the elongate shaft (10).
6. The device (1) according to any one of the preceding
aspects, wherein the elongate shaft (10) has a length
between 10 mm to 2000 mm, optionally between 50
mm to 500 mm, optionally between 100 mm to 200
mm.
7. The device (1) according to any one of the preceding
aspects, wherein the elongate shaft (10) is rigid and/or
wherein the elongate shaft (10) is straight along the
longitudinal axis (A$_L$).
8. The device (1) according to any one of the preceding
aspects, wherein the elongate shaft (10) has a diameter
smaller than 15 mm, optionally a diameter smaller than
7 mm, optionally a diameter smaller than 4 mm.
9. The device (1) according to any one of the preceding
aspects, wherein the elongate shaft (10) comprises a
lumen (15) extending along the longitudinal axis (A$_L$).
10. The device (1) according to the preceding aspect,
wherein the lumen (15) has a diameter smaller than 10
mm, optionally a diameter smaller than 7 mm, option-
ally a diameter smaller than 4 mm.
11. The device (1) according to any of the preceding two
aspects, wherein the lumen (15) has a diameter larger
than 0.1 mm, optionally a diameter larger than 0.25
mm, optionally a diameter larger than 0.5 mm.

12. The device (1) according to any of the preceding three aspects, wherein the lumen (15) extends from the proximal end (11) to the distal end (12) of the elongate shaft (10).

13. The device (1) according to any one of the preceding aspects, wherein the elongate shaft (10) is made from a mechanically stiff material with an elastic modulus of ca. 210 GPa, optionally from a metallic material such as stainless steel or fibre reinforced polymers.

14. The device (1) according to any one of the preceding aspects, wherein the device (1) further comprises a handle at the proximal end (11) of the elongate shaft (10).

15. The device (1) according to any one of the preceding aspects, wherein the device (1) further comprises at least one actuator, optionally a plurality of actuators, at the proximal end (11) of the elongate shaft (10), optionally at the handle.

16. The device (1) according to any one of the preceding aspects, wherein a distal end of the device (1), optionally the distal end (12) of the elongate shaft (10), is atraumatic.

17. The device (1) according to any one of the preceding aspects, wherein the longitudinal axis ($A_L$) of the elongate shaft (10) is configured to be oriented substantially perpendicular to the tissue (100) when closing the tissue opening (101).

18. The device (1) according to any one of the preceding aspects, wherein the elongate shaft (10) comprises at least three needle guides (13), optionally at least four needle guides (13).

19. The device (1) according to any one of the preceding aspects, wherein the needle guides (13) have a diameter smaller than 2 mm, optionally a diameter smaller than 1 mm, optionally a diameter smaller than 0.5 mm.

20. The device (1) according to any one of the preceding aspects, wherein the needle guides (13) have a diameter larger than 0.1 mm, optionally a diameter larger than 0.2 mm, optionally a diameter larger than 0.4 mm.

21. The device (1) according to any one of the preceding aspects, wherein the exit openings (14) are spaced at least 3 mm, optionally at least 8 mm in the proximal direction from a proximally facing side of the support structure (20) that is pressed against the second tissue layer (104) when the support structure (20) is in the second, expanded configuration.

22. The device (1) according to any one of the preceding aspects,
   wherein the exit openings (14) are located proximal of a position at which the support structure (20) is movably coupled to the elongate shaft (10), optionally proximal from a most proximal position at which the support structure (20) is movably coupled to the elongate shaft (10); or
   wherein the exit openings (14) are located distal from a position at which the pushing member (80) is movably coupled to the elongate shaft (10), optionally distal from a most proximal position at which the pushing member (80) is movably coupled to the elongate shaft (10).

23. The device (1) according to any one of the preceding aspects, wherein each of the needle guides (13) has a first portion (16) and a second portion (17), the second portion (17) extending obliquely to the longitudinal axis ($A_L$), optionally wherein the first portion (16) is substantially parallel to the longitudinal axis ($A_L$).

24. The device (1) according to the preceding aspect, wherein the second portion (17) forms a distal portion of the respective needle guide (13).

25. The device (1) according to any of the two preceding aspects, wherein each of the needle guides (13) comprises a curved segment, optionally wherein the curved segment is located between the first portion (16) and the second portion (17) and/or wherein the second portion (17) is curved.

26. The device (1) according to any of the three preceding aspects, wherein the second portion (17) extends at least partially around the longitudinal axis ($A_L$).

27. The device (1) according to any one of the preceding aspects,
   wherein each of the needle guides (13) is configured such that the trajectory along which the respective needle (30, 40) extends from the exit opening (14) extends at an angle ($\alpha$) to the longitudinal axis ($A_L$), optionally;
   wherein the angle ($\alpha$) is at most 50°, optionally at most 30°; and/or
   wherein the angle ($\alpha$) is at least 5°, optionally at least 10°.

28. The device (1) according to any one of the preceding aspects, wherein the elongate shaft (10) comprises at least three exit openings (14), optionally at least four exit openings (14), optionally wherein the exit openings (14) are spaced around a periphery of the elongate shaft (10), optionally wherein the exit openings (14) are spaced at regular intervals around the periphery of the elongate shaft (10).

29. The device (1) according to any one of the preceding aspects, wherein the exit openings (14) are located along a peripheral side surface of the elongate shaft (10).

30. The device (1) according to any one of aspects 1-28, wherein the exit openings (14) are located in a distally facing surface of the elongate shaft (10), optionally wherein the exit openings (14) are located distal from a first position at which the pushing member (80) and/or the guide member (90) is movably coupled to the elongate shaft (10), optionally distal from a most proximal position at which the pushing member (80) and/or the guide member (90) is movably coupled to the elongate shaft (10), and/or optionally wherein the exit openings (14) are located proximal from a second position at which the pushing member (80) is movably coupled to the elongate shaft (10), optionally proximal from a most distal position at which the pushing member (80) and/or the guide member (90) is movably coupled to the elongate shaft (10).

31. The device (1) according to any one of the preceding aspects, wherein each needle guide (13) has an entry opening at its proximal end.

32. The device (1) according to any one of the preceding aspects, wherein the elongate shaft (10) comprises two or more entry openings, optionally four entry openings.

33. The device (1) according to any one of the preceding aspects, wherein the entry openings are located along an outer side surface of the elongate shaft (10).

34. The device (1) according to any one of the preceding aspects, wherein the needles (30, 40) are pre-mounted in their respective needle guides (13).

35. The device (1) according to any one of the preceding aspects, wherein the support structure (20) in the first, contracted configuration is configured to be inserted through the tissue opening (101) into the body cavity (105).

36. The device (1) according to any one of the preceding aspects,
wherein the support structure (20) in the first, contracted configuration does not radially extend beyond an outer diameter of the elongate shaft (10); and/or
wherein the support structure (20) in the first, contracted configuration has a diameter of 10 mm or less, optionally 5 mm or less.

37. The device (1) according to any one of the preceding aspects, wherein the support structure (20) in the second, expanded configuration is configured to be pressed against the second tissue layer (104), optionally from within the cavity (105) in a proximal direction, optionally by pulling the elongate shaft in the proximal direction.

38. The device (1) according to any one of the preceding aspects,
wherein the support structure (20) in the second, expanded configuration extends beyond the outer diameter of the elongate shaft (10), and/or
wherein the support structure (20) in the second, expanded configuration has a diameter of at least 5 mm, optionally at least 8 mm.

39. The device (1) according to any one of the preceding aspects, wherein the support structure (20) in the second, expanded configuration is configured such that the at least one first connector (61) and the at least one second connector (62) are disposed on opposite sides of and/or around the tissue opening (101) in the body cavity (105).

40. The device (1) according to any one of the preceding aspects, wherein the support structure (20) is configured to switch between the first, contracted configuration and the second, expanded configuration by pushing and pulling the elongate shaft (10) along the longitudinal axis ($A_L$), respectively.

41. The device (1) according to any one of the preceding aspects, wherein the device (1) further comprises at least one first actuation member (63) extending along the elongate shaft (10), optionally wherein the first actuation member (63) is a wire, a rod, a sleeve or a tube, the first actuation member (63) being movable along the longitudinal axis ($A_L$), wherein the support structure (20) is coupled to the first actuation member (63), optionally to a distal end thereof, optionally:
wherein the support structure (20) is moved to the contracted configuration by pushing the first actuation member (63) in the distal direction with respect to the elongate shaft (10) and to the expanded configuration by pulling the first actuation member (63) in the proximal direction with respect to the elongate shaft (10); or
wherein the support structure (20) is moved to the contracted configuration by pulling the first actuation member (63) in the distal direction with respect to the elongate shaft (10) and to the expanded configuration by pushing the first actuation member (63) in the proximal direction with respect to the elongate shaft (10).

42. The device (1) according to any one of the preceding aspects, wherein the support structure (20) comprises a membrane cover and/or one or more inflatable members.

43. The device (1) according to any one of the preceding aspects, wherein the support structure (20) comprises at least one support arm (21), optionally a plurality of support arms (21) such as two, at least three, four or at least four support arms (21), optionally wherein a first end of each support arm (21) is movably connected to one of the elongate shaft (10) and the first actuation member (63), optionally by a first hinge.

44. The device (1) according to the preceding aspect, wherein one or more pairs of the support arms (21) are configured to expand on diametrically opposite sides of the elongate shaft (10).

45. The device (1) according to any one of the preceding aspects, wherein the support structure (20) further comprises a plurality of support links (22), optionally two, at least three, four or at least four support links (22).

46. The device (1) according to the preceding aspect, wherein each of the support arms (21) is connected to a respective support link (22) by a movable joint, optionally a second hinge.

47. The device (1) according to the preceding aspect, wherein a second end of each of the support arms (21) is connected to a first end of the respective support link (22) by the movable joint.

48. The device (1) according to the preceding aspect, wherein a second end of the respective support link (22) is movably connected to the other one of the elongate shaft (10) and the first actuation member (63), optionally by a third hinge.

49. The device (1) according to any of the preceding four aspects, wherein each of the support arms (21) and/or each of the support links (22) in the first, contracted configuration are substantially parallel to the longitudinal axis ($A_L$).

50. The device (1) according to any of the preceding five aspects, wherein each of the support arms (21) in the second, expanded configuration is substantially perpendicular to the longitudinal axis ($A_L$), and wherein each of the support links (22) in the second, expanded configuration is oblique to the longitudinal axis ($A_L$).

51. The device (1) according to any of the preceding six aspects, wherein each of the support arms (21) comprises a retainer (23) for releasably retaining a respective one of the at least one first connector (61) and the at least one second connector (62) therein, optionally wherein each support arm (21) comprises a release opening (24) or slot for releasing the suture (50, 60, 70) from the support arm (21).

52. The device (1) according to the preceding aspect, wherein each retainer (23) is positioned at least 2 mm, optionally at least 5 mm, radially away from the longitudinal axis ($A_L$) when the support structure (20) is in the second, expanded configuration.

53. The device (1) according to any of the two preceding aspects, wherein the retainers (23) are configured to release the connector (61, 62) retained therein when a pushing or pulling force on the connector (61, 62) exceeds a predetermined threshold, optionally wherein:
at least one retainer (23), optionally the retainer (23) of the first connector (61), is configured to release the connector (61, 62) retained therein when a distal pushing force applied on the connector (61, 62) by the respective needle (30) exceeds a predetermined threshold and at least another retainer (23), optionally the retainer (23) of the second connector (62), is configured to release the connector (61, 62) retained therein when a proximal pulling force applied on the connector (61, 62) by the respective needle (40) exceeds a predetermined threshold; or wherein the retainers (23) of the first and second connectors (61, 62) are configured to release the connector (61, 62) retained therein when a proximal pulling force applied by the respective needles (30, 40) exceeds a predetermined threshold.

54. The device (1) according to any of the three preceding aspects, wherein one or more of the retainers (23) are surrounded by a funnel-shaped guiding surface configured to guide the respective needle (30, 40) into the respective connector (61, 62).

55. The device (1) according to any one of the preceding aspects, wherein the shaft (10) is provided with one or more pockets at its distal end (12), wherein the one or more pockets are configured for receiving the support structure (20), in particular one or more of the support links (22) when the device is in the first, contracted configuration.

56. The device (1) according to any one of the preceding aspects, further comprising at least one first suture (60), thread or wire that is coupled to the first and second connectors (61, 62).

57. The device (1) according to the preceding aspect, wherein the at least one first suture (60), thread or wire has a diameter smaller than 0.6 mm, optionally a diameter smaller than 0.4 mm, optionally a diameter smaller than 0.25 mm.

58. The device (1) according to any of the two preceding aspects, wherein the at least one first suture (60), thread or wire has a length of 50 mm or less, optionally 30 mm or less, optionally 15 mm or less.

59. The device (1) according to any of the three preceding aspects, wherein the at least one first suture (60), thread or wire is configured to be withdrawn from the tissue during use of the device (1).

60. The device (1) according to aspect 56 or 57, wherein a length of the first suture (60), thread or wire is stored in a cavity and/or cartridge that is arranged at the distal end of the elongate shaft (10), optionally wherein the cavity or cartridge comprises a spool onto which at least part of the length of the first suture (60), thread or wire is wound.

61. The device (1) according to aspect 56 or 57, wherein the elongate shaft (10) and/or the first actuation member (63) comprises a lumen (15) and a length of the first suture (60), thread or wire is stored in the lumen (15), optionally wherein:

the elongate shaft (10) or the first actuation member (63) comprises at least one distal opening through which the first suture (60), thread or wire enters into the lumen (15); and/or the length of the first suture (60), thread or wire is stored in the lumen (15) and/or outside of a proximal end of the lumen (15) as at least one loop; and/or the first suture (60), thread or wire extends through the lumen (15) along the longitudinal axis ($A_L$).

62. The device (1) according to any one of the two preceding aspects, wherein the length of the first suture (60) is at least 60 mm, optionally at least 400 mm.

63. The device (1) according to any one of the three preceding aspects, wherein the at least one suture (50; 60; 70), thread or wire is configured to remain in the tissue (100) after the device (1) is withdrawn.

64. The device (1) according to any of the eight preceding aspects, wherein the at least one suture (50; 60; 70)

further comprises at least one washer (64), optionally two or at least four washers (64), configured to remain in the tissue (100) and to cover the stitching holes penetrated by the first and second needles (30; 40), optionally wherein the at least one washer (64) is pre-arranged on the at least one first suture (60).

65. The device (1) according to the preceding aspect, wherein the one or more washers (64) are arranged on the suture (50; 60; 70) in such manner that they are located within the body cavity (105) after the tissue opening (101) is closed, optionally in abutment against the tissue (100), in particular in abutment against the second tissue layer (104).

66. The device (1) according to any one of the two preceding aspects, wherein the one or more washers (64) have a diameter of less than 3 mm, optionally less than 2 mm, and/or wherein the one or more washers (64) have a thickness of less than 2 mm, optionally less than 1 mm.

67. The device (1) according to any one of the three preceding aspects, wherein the at least one suture (50; 60; 70) may comprise at least one patch that is configured to remain in the body cavity (105) and overlap with the closed tissue opening (101) from within the cavity (105), optionally wherein the at least one patch is elastic and/or resorbable.

68. The device (1) according to any one of the twelve preceding aspects, wherein the support structure (20) comprises at least one groove or channel (25) configured to releasably retain and/or guide the first suture (60), thread or wire therein, optionally wherein the support structure (20) is configured to hold the suture taut in the groove or channel (25; 25A) when in the first, contracted configuration and/or when in the second, expanded configuration.

69. The device (1) according to the preceding aspect, wherein the groove or channel (25) comprises a first width in cross section, and wherein the support structure (20) further comprises a slot for releasing the first suture form the groove or channel (25), wherein the slot comprises a second width in cross section that is less than the first width.

70. The device (1) according to any one of the two preceding aspects, wherein the support structure comprises a plurality of grooves or channels (25) that are spaced apart from each other.

71. The device (1) according to any one of the three preceding aspects, wherein the one or more grooves or channels (25; 25A; 25B) are provided along one or more of the support arms (21) and/or support links (22), optionally on a side of the respective support arms (21) and/or support links (22) that face in the distal direction when the support structure (20) is in the second, expanded configuration, optionally at least partially extending in a structure protruding from the respective support arms (21) and/or support links (22).

72. The device (1) according to any one of the preceding aspects, wherein the at least one first needle (30) and the at least one second needle (40) are configured to move separately.

73. The device (1) according to any one of the preceding aspects, wherein the first needle (30) and the second needle (40) have a sharp distal end.

74. The device (1) according to any one of the preceding aspects, wherein the at least one first needle (30) and/or the at least one second needle (40) is made from a metallic material, optionally nitinol, stainless steel or titanium.

75. The device (1) according to any one of the preceding aspects, wherein the first needle (30) and the second needle (40) has an outer diameter smaller than 2 mm, optionally an outer diameter smaller than 1 mm, more preferably an outer diameter smaller than 0.5 mm.

76. The device (1) according to any one of the preceding aspects, wherein
   the second needle (40) is a hollow needle comprising a second needle lumen extending therethrough, optionally wherein the first needle (30) is a solid needle that is devoid of a needle lumen extending therethrough.

77. The device (1) according to any of the preceding aspects, wherein the at least one second needle (40) has a releasable tip (51).

78. The device (1) according to the preceding aspect, wherein a second suture (50), thread or wire is coupled to the releasable tip (51), optionally wherein the second suture (50), thread or wire extends at least partially through the second needle lumen and/or the second needle guide (13).

79. The device (1) according to the preceding aspect, wherein the second suture (50), thread or wire is configured to be pulled through the at least one second needle (40) and/or wherein the second suture (50), thread or wire is configured to be pulled through the elongate shaft (10).

80. The device (1) according to any of the two preceding aspects, wherein the second suture (50), thread or wire extends along the elongate shaft (10) towards the proximal end (11) of the elongate shaft (10), optionally wherein the second suture (50), thread or wire remains accessible to a user outside a body of a patient being treated for connecting a further suture (70) thereto.

81. The device (1) according to any of the three preceding aspects, wherein the at least one second suture (50), thread or wire has a diameter smaller than 0.5 mm, optionally a diameter smaller than 0.35 mm, optionally a diameter smaller than 0.2 mm.

82. The device (1) according to any of the five preceding aspects, wherein the releasable tip (51) is configured to be coupled with and retained by the second connector (62), optionally via a form fit or a press fit coupling.

83. The device (1) according to any of the six preceding aspects, wherein the releasable tip (51) comprises an undercut and/or a barbed hook for coupling with the second connector (62).

84. The device (1) according to any of the seven preceding aspects, wherein the first needle is configured to retract the first and second connectors (61, 62) in a proximal direction through the needle guide (13) of the first needle (30).

85. The device (1) according to any one of the preceding aspects, wherein the at least one first needle (30) and the at least one second needle (40) are respectively a hollow needle each comprising a needle lumen extending therethrough configured to inject fluids from a needle hole, optionally growth factors or glue, into the tissue (100).

86. The device (1) according to any one of aspects 1-75, wherein the at least one first needle (30) is configured to retract the first connector (61) in a proximal direction through the needle guide (13) of said first needle (30), and the at least one second needle (40) is configured to retract the second connector (62) in a proximal direction through the needle guide (13) of said second needle (40).

87. The device (1) according to any one of aspects 1-75 or 86, wherein the first needle (30) and/or the second needle (40) are solid needles that are devoid of a needle lumen extending therethrough.

88. The device (1) according to any one of the preceding aspects, wherein the device (1) comprises at least two first needles (30) and at least two second needles (40).

89. The device (1) according to any one of the preceding aspects,
   wherein the at least one pushing member (80) in the contracted configuration does not radially extend beyond an outer diameter of the elongate shaft (10).

90. The device (1) according to any one of the preceding aspects,
   wherein the at least one pushing member (80) when expanded is configured to lift the first tissue layer (103) away from the second tissue layer (104) in a proximal direction; and/or
   wherein the at least one pushing member (80) is configured to push the first tissue layer (103) away from the device (1) perpendicularly to the longitudinal axis (A$_L$) in a radially outward direction.

91. The device (1) according to any one of the preceding aspects,
   wherein the at least one pushing member (80) is expandable together with the support structure (20), optionally wherein the at least one pushing member (80) is coupled to the first actuation member (63); or
   wherein the at least one pushing member (80) is expandable independently of the support structure (20).

92. The device (1) according to any one of the preceding aspects, wherein the device (1), optionally a handle thereof, is configured such that the at least one pushing member (80) can only be moved to its expanded configuration once the support structure (20) is moved to its expanded configuration.

93. The device (1) according to any one of the preceding aspects, wherein, in the expanded configuration,
   the at least one pushing member (80) is located at least 2 mm away, optionally at least 5 mm away, from the distal end (12) of the elongate shaft (10); and/or
   the at least one pushing member (80) is located at most 100 mm away, optionally at most 20 mm away, from the distal end (12) of the elongate shaft (10).

94. The device (1) according to any one of the preceding aspects, wherein the at least one pushing member (80) comprises a membrane cover, optionally wherein the membrane cover covers the pushing member (80) from the proximal direction.

95. The device (1) according to any one of the preceding aspects, wherein the at least one pushing member (80) comprises a plurality of flaps (81), optionally two or at least four flaps (81).

96. The device (1) according to the preceding aspect, wherein a first end of each of the flaps (81) is movably connected to one of the elongate shaft (10), the first actuation member (63) and a second actuation member, optionally by a hinge.

97. The device (1) according to any one of the preceding aspects, wherein the at least one pushing member (80) comprises a plurality of pushing member links (82), optionally two or at least four pushing member links (82), optionally at least one pushing member link (82) for each flap (81).

98. The device (1) according to the preceding aspect, wherein each of the flaps (81) is connected to a respective pushing member link (82) by a movable joint, optionally a hinge.

99. The device (1) according to the preceding aspect, wherein a second end of each of the flaps (81) is connected to a first end of a respective pushing member link (82) by the movable joint.

100. The device (1) according to the preceding aspect, wherein a second end of the respective pushing member link (82) is movably connected to one of the first actuation member (63), a second actuation member or the elongate shaft (10), optionally by a hinge.

101. The device (1) according to any one of the preceding aspects, wherein the device (1) further comprises at least one second actuation member extending along the elongate shaft (10), the second actuation member being movable along the longitudinal axis (A$_L$) between a first position and a second position, optionally wherein the first position is a distally advanced position and the second position is a proximally retracted position.

102. The device (1) according to the preceding aspect, wherein the pushing member (80) is moved to the contracted configuration by moving the second actuation member to the first position and to the expanded configuration by moving the second actuation member to the second position, or vice versa.

103. The device (1) according to any of the two preceding aspects, wherein the second actuation member is a wire, a rod, a sleeve or a tube (83).

104. The device (1) according to any of the three preceding aspects, wherein the second actuation member is configured to maintain the pushing member (80) in the contracted configuration by at least partially covering the flaps (81) when in the first position, and wherein the second actuation member allows the flaps (81) to move to the expanded configuration when in the second position, optionally wherein the second actuation member is a sleeve (83).

105. The device (1) according to any of the four preceding aspects, wherein the second actuation member is configured to move the flaps (81) radially outward when in the second position.

106. The device (1) according to the preceding aspect, wherein a portion of the second actuation member is disposed between the flaps (81) and the elongate shaft (10) when the second actuation member is in the second position.

107. The device (1) according to any of the six preceding aspects, wherein the flaps (81) are biased towards a radially outward, expanded configuration, optionally wherein the flaps (81) are made from an elastic material and/or wherein the flaps (81) are connected to the elongate shaft (10) by a spring hinge.

108. The device (1) according to any one of the seven preceding aspects, wherein each of the flaps (81) is coupled to the second actuation member, or to a respective second actuation member, at a position that is eccentric to an axis around which the respective flap (81) rotates when moving the pushing member (80) from the contracted configuration to the expanded configuration.

109. The device (1) according to any one of the preceding aspects, wherein the at least one pushing member (80), optionally the at least one flap (81), comprises at least one marker for determining the configuration of the pushing member in a medical imaging procedure, optionally wherein the marker is an ultrasound marker and/or a radiopaque material.

110. The device (1) according to any one of the preceding aspects, wherein the at least one pushing member (80), optionally the at least one flap (81), is made from an ultrasound visible material and/or a radiopaque material, optionally wherein the support structure (20), optionally the at least one support arm (21), is made from an ultrasound visible material and/or a radiopaque material.

111. The device (1) according to any one of the preceding aspects, wherein the at least one pushing member (80) is provided as or comprises an inflatable structure, for example an inflatable balloon.

112. The device (1) according to the preceding aspect, wherein the flaps (81) are expanded by inflating the inflatable structure, for example with a gas or a liquid.

113. The device (1) according to any one of aspects 2 to 112, wherein the at least one expandable guide member (90) in the contracted configuration does not radially extend beyond an outer diameter of the elongate shaft (10).

114. The device (1) according to any one of aspects 2 to 113, wherein the at least one expandable guide member (90) comprises at least one guide opening (91), which in the expanded configuration overlaps with the first or second trajectory, optionally at least one first guide opening (91) that overlaps with the first trajectory and at least one second guide opening (91) that overlaps with the second trajectory.

115. The device (1) according to the preceding aspect, wherein the at least one guide opening (91) comprises a release opening or release slot for releasing the suture (50, 60, 70) from the guide opening (91), optionally wherein the release opening or release slot extends to a periphery of the guide member (90) and is open at the periphery of the guide member (90), optionally wherein the release opening or release slot extends from the guide opening (91) in a radially inward direction.

116. The device (1) according to any of the two preceding aspects, wherein the at least one guide opening (91) has a width and/or diameter smaller than 2 mm, optionally smaller than 1 mm, optionally smaller than 0.5 mm.

117. The device (1) according to any one of the three preceding aspects, wherein the at least one guide opening (91) has length smaller than 2 mm, optionally smaller than 0.5 mm along the first and/or second trajectories in the expanded configuration.

118. The device (1) according to any one of the four preceding aspects, wherein
   the at least one guide opening (91) is located at least 2 mm away, optionally at least 3 mm away, from the longitudinal axis (A$_L$); and/or
   the at least one guide opening (91) is located at most 8 mm away, optionally at most 5 mm away, from the longitudinal axis (A$_L$)

119. The device (1) according to any one of the five preceding aspects, wherein the at least one guide opening (91) is located at least 1.5 mm away, optionally at least 3 mm away, from the distal end (12) of the elongate shaft (10); and/or wherein the at least one guide opening (91) is located at most 80 mm away, optionally at most 15 mm away, from the distal end (12) of the elongate shaft (10).

120. The device (1) according to any one of the six preceding aspects, wherein the guide opening (91) is surrounded by a funnel-shaped guiding surface configured to guide a respective needle (30, 40) into the guide opening (91).

121. The device (1) according to any one of aspects 2 to 120, wherein the at least one expandable guide member (90) comprises a membrane cover.

122. The device (1) according to any one of aspects 2 to 121, wherein the at least one guide member (90) is connected to the elongate shaft (10) by at least one hinge, optionally wherein the at least one guide member (90) comprises a plurality of arms (82), each of which is hinged to the elongate shaft (10).

123. The device (1) according to any one of aspects 97 to 122, wherein the at least one expandable guide member (90) is formed by one or more of the plurality of pushing member links (82).

124. The device (1) according to any one of aspects 95 to 123, wherein the at least one expandable guide member (90) is formed by the at least one pushing member flap (81) or by a plurality of pushing member flaps (81).

125. A device (1) for closing a tissue opening (101) in a tissue (100) with at least one suture (50, 70), the tissue extending at least partially around a body cavity (105) and comprising at least first and second tissue layers (103, 104), the second tissue layer (104) extending between the first tissue layer (103) and the body cavity (105), the device (1) comprising:

an elongate shaft (10) having a proximal end (11), a distal end (12) and extending along a longitudinal axis ($A_L$), the elongate shaft (10) configured to be inserted into the tissue opening (101), the elongate shaft (10) comprising a plurality of needle guides (13), each needle guide (13) having an exit opening (14) at its distal end;

a support structure (20) at the distal end (12) of the elongate shaft (10) configured to move between a first, contracted configuration and a second, expanded configuration, the support structure (20) comprising at least one support arm (21), the support structure (20) being configured to be expanded in the body cavity (105);

at least one first needle (30) and at least one second needle (40);

at least one first connector (61) and at least one second connector (62) releasably coupled to the support structure (20) such that the first and second connectors (61; 62) are disposed on opposite sides of and/or around the tissue opening (101) in the body cavity (105) in the second, expanded configuration, the first connector (61) being configured to couple with a distal end of the first needle (30) and the second connector (62) being configured to couple with a releasable tip (51) of the second needle (40);

wherein each of the needles (30, 40) is configured to be translated along a respective one of the needle guides (13), the first needle (30) is configured to be advanced out of the exit opening (14) of the respective needle guide (13) and to penetrate through the second tissue layer (104) along a first trajectory, the first trajectory extending from the exit opening (14) through the second tissue layer (104) obliquely to the longitudinal axis ($A_L$) to the first connector (61), and the second needle (40) is configured to be advanced out of the exit opening (14) and to penetrate through the second tissue layer (104) along a second trajectory, the second trajectory extending from the exit opening (14) through the second tissue layer (104) obliquely to the longitudinal axis ($A_L$) to the second connector (62);

at least one auxiliary suture (60), thread or wire coupled to the at least one first connector (61) and the at least one second connector (62); and at least one further suture, thread or wire (50), the at least one further suture, thread or wire (50) being coupled to the releasable tip (51) and extending along the elongate shaft (10) and/or along the second needle (40).

126. A device (1) for closing a tissue opening (101) in a tissue (100) with at least one suture (60, 70), the tissue extending at least partially around a body cavity (105) and comprising at least first and second tissue layers (103, 104), the second tissue layer (104) extending between the first tissue layer (103) and the body cavity (105), the device (1) comprising:

an elongate shaft (10) having a proximal end (11), a distal end (12) and extending along a longitudinal axis ($A_L$), the elongate shaft (10) configured to be inserted into the tissue opening (101), the elongate shaft (10) comprising a plurality of needle guides (13), each needle guide (13) having an exit opening (14) at its distal end;

a support structure (20) at the distal end (12) of the elongate shaft (10) configured to move between a first, contracted configuration and a second, expanded configuration, the support structure (20) comprising at least one support arm (21), the support structure (20) being configured to be expanded in the body cavity (105);

at least one first needle (30) and at least one second needle (40);

at least one first connector (61) and at least one second connector (62) releasably coupled to the support structure (20) such that the first and second connectors (61) are disposed on opposite sides of and/or around the tissue opening (101) in the body cavity (105) in the second, expanded configuration, the first connector (61) being configured to couple with a distal end of the first needle (30) and the second connector (62) being configured to couple with a distal end of the second needle (40);

wherein each of the needles (30, 40) is configured to be translated along a respective one of the needle guides (13), the first needle (30) is configured to be advanced out of the exit opening (14) of the respective needle guide (13) and to penetrate through the second tissue layer (104) along a first trajectory, the first trajectory extending from the exit opening (14) through the second tissue layer (104) obliquely to the longitudinal axis ($A_L$) to the first connector (61), and the second needle (40) is configured to be advanced out of the exit opening (14) and to penetrate through the second tissue layer (104) along a second trajectory, the second trajectory extending from the exit opening (14) through the second tissue layer (104) obliquely to the longitudinal axis ($A_L$) to the second connector (62);

at least one suture (60), thread or wire coupled to the at least one first connector (61) and the at least one second connector (62); and optionally wherein at least a portion of the at least one suture (60), thread or wire is stored within a lumen, a cavity or a cartridge of the device.

127. A method for suturing an opening in a tissue using the device according to any of the preceding aspects.

Although the present invention has been described with reference to preferred embodiments, workers skilled in the art will recognize that changes may be made in form and detail without departing from the spirit and scope of the invention.

The invention claimed is:

1. A device for closing a tissue opening in a tissue with at least one suture, the tissue extending at least partially around a body cavity and comprising at least first and second tissue layers, the second tissue layer extending between the first tissue layer and the body cavity, the device comprising:

an elongate shaft having a proximal end, a distal end and extending along a longitudinal axis, the elongate shaft configured to be inserted into the tissue opening in the tissue, the elongate shaft comprising a plurality of needle guides, each needle guide having an exit opening at its distal end;

a support structure at the distal end of the elongate shaft configured to move between a first, contracted configuration and a second, expanded configuration the support structure being configured to be expanded in the body cavity;

at least one first needle and at least one second needle;

at least one first connector and at least one second connector coupled to the support structure, the first connector being configured to couple with the first needle;

at least one first suture, thread or wire that is coupled to the first and second connectors, wherein a length of the first suture, thread or wire is stored in a lumen, a cavity or a cartridge of the device, and wherein the length of the first suture, thread or wire stored in the lumen, cavity or cartridge of the device is at least 60 mm;

wherein each of the needles is configured to be translated along a respective one of the needle guides, the first needle being configured to be advanced out of the exit opening of the respective needle guide and to penetrate through the second tissue layer along a first trajectory, the first trajectory extending from the exit opening through the second tissue layer obliquely to the longitudinal axis to the first connector, and the second needle being configured to be advanced out of the exit opening of the respective needle guide and to penetrate through the second tissue layer along a second trajectory, the second trajectory extending from the exit opening through the second tissue layer obliquely to the longitudinal axis to the second connector; and at least one expandable pushing member configured to push the first tissue layer out of the first and second trajectories, the pushing member being configured to move between a contracted configuration and an expanded configuration, wherein the first and second trajectories are partially in a cavity created between the pushing member and the elongate shaft.

2. The device according to claim 1, wherein the elongate shaft comprises at least one distal opening through which the first suture enters into the lumen, and wherein the length of the first suture, thread or wire is stored in the lumen as at least one loop.

3. The device according to claim 1, wherein the support structure in the second, expanded configuration is configured such that the first connector and the second connector are disposed on opposite sides of the tissue opening in the body cavity.

4. The device according to claim 1, wherein the device comprises at least one expandable guide member configured to guide the at least one first and the at least one second needles along their respective trajectory, the guide member being configured to move between a contracted configuration and an expanded configuration, wherein the guide member overlaps with the first and second trajectories in the expanded configuration.

5. The device according to claim 4, wherein the at least one expandable guide member comprises at least one guide opening, which in the expanded configuration overlaps with the first or second trajectory.

6. The device according to claim 4, wherein at least one first guide opening overlaps with the first trajectory and at least one second guide opening overlaps with the second trajectory.

7. The device according to claim 4, wherein the at least one expandable guide member is formed by one or more of a plurality of pushing member links.

8. The device according to claim 4, wherein the at least one expandable guide member is formed by at least one pushing member flap or by a plurality of pushing member flaps.

9. The device according to claim 1, wherein the support structure in the first, contracted configuration is configured to be inserted through the tissue opening into the body cavity, and wherein the support structure in the second, expanded configuration is configured to be pressed against the second tissue layer from within the cavity in a proximal direction.

10. The device according to claim 1, wherein the support structure comprises at least two support arms, and wherein each of the support arms comprises a retainer for releasably retaining a respective one of the at least one first connector and the at least one second connector therein.

11. The device according to claim 10, wherein each support arm comprises a release opening or slot for releasing the suture from the support arm.

12. The device according to claim 1, wherein the at least one first suture, thread or wire is configured to be withdrawn from the tissue during use of the device.

13. The device according to claim 12, wherein at least one of the support structure and a distal tip of the device comprises at least one groove or channel configured to releasably retain the first suture, thread or wire therein.

14. The device according to claim 1, wherein the second needle is a hollow needle comprising a second needle lumen extending therethrough;

wherein the at least one second needle has a releasable tip;

wherein a second suture, thread or wire is coupled to the releasable tip; and wherein the releasable tip is configured to be coupled with and retained by the second connector.

15. The device according to claim 14, wherein the first needle is a solid needle that is devoid of a needle lumen extending therethrough.

16. The device according to claim 14, wherein the second suture, thread or wire extends at least partially through at least one of the second needle lumen and the second needle guide.

17. The device according to claim 14, wherein the releasable tip is configured to be coupled with and retained by the second connector via at least one of form fit coupling and press fit coupling.

18. The device according to claim 1, wherein the first needle is configured to retract the first and second connectors in a proximal direction through the needle guide of the first needle.

19. The device according to claim 1, wherein the device further comprises at least one first actuation member extending along the elongate shaft, the first actuation member being movable along the longitudinal axis, wherein the support structure is coupled to the first actuation member, and wherein the lumen extends from a distal opening into the elongate shaft.

20. The device according to claim 19, wherein the first actuation member is a wire, a rod, a sleeve or a tube.

21. The device according to claim 19, wherein the distal opening is at the distal end, and wherein the at least one first suture, thread or wire extends out of the distal opening and to the first and second connectors.

22. The device according to claim 1, wherein the device comprises at least two first needles and at least two second needles.

23. The device according to claim 1, wherein the at least one pushing member is configured to lift the first tissue layer away from the second tissue layer in a proximal direction.

24. The device according to claim 23, wherein, in the expanded configuration, the at least one pushing member is located at least 2 mm away from the distal end of the elongate shaft.

25. The device according to claim 23, wherein, in the expanded configuration, the at least one pushing member is located at most 100 mm away, from the distal end of the elongate shaft.

26. The device according to claim 1, wherein the at least one pushing member is configured to push the first tissue layer away from the device perpendicularly to the longitudinal axis in a radially outward direction.

27. The device according to claim 1, wherein the at least one pushing member comprises a plurality of flaps.

* * * * *